(12) United States Patent
Miyake et al.

(10) Patent No.: US 11,104,653 B2
(45) Date of Patent: Aug. 31, 2021

(54) METHODS FOR FORMING ARYL CARBON-NITROGEN BOND USING LIGHT

(71) Applicant: Colorado State University Research Foundation, Fort Collins, CO (US)

(72) Inventors: Garret Miyake, Fort Collins, CO (US); Chern-Hooi Lim, Fort Collins, CO (US); Max Kudisch, Fort Collins, CO (US); Bin Liu, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 16/404,255

(22) Filed: May 6, 2019

(65) Prior Publication Data

US 2019/0345122 A1  Nov. 14, 2019

Related U.S. Application Data

(60) Provisional application No. 62/668,515, filed on May 8, 2018.

(51) Int. Cl.
*C07D 295/073* (2006.01)
*C07D 211/62* (2006.01)
(Continued)

(52) U.S. Cl.
CPC ........ *C07D 295/073* (2013.01); *B01J 19/123* (2013.01); *B01J 27/08* (2013.01);
(Continued)

(58) Field of Classification Search
CPC ... C07C 209/60; C07C 211/45; C07C 211/48; C07C 211/56; C07C 209/68;
(Continued)

(56) References Cited

U.S. PATENT DOCUMENTS

| 8,716,697 B2 | 5/2014 | Herron et al. |
| 2008/0033171 A1 | 2/2008 | Buchwald et al. |
| 2018/0370911 A1 | 12/2018 | Miyake et al. |

FOREIGN PATENT DOCUMENTS

| WO | 2006/074315 A2 | 7/2006 |
| WO | 2016/196816 A1 | 12/2016 |

OTHER PUBLICATIONS

Corcoran et al. (Science 353, 279-283 (2016)).*
(Continued)

*Primary Examiner* — Valerie Rodriguez-Garcia
(74) *Attorney, Agent, or Firm* — Polsinelli PC

(57) ABSTRACT

The disclosure relates to a method for forming aryl carbon-nitrogen bonds and to photoreactors useful in these and other light-driven reactions. The method comprises contacting an aryl halide, such as 4-bromobenzotrifluoride, with an amine, such as morpholine, in the presence of a Ni salt catalyst solution and an optional base, thereby forming a reaction mixture; exposing the reaction mixture to light under reaction condition sufficient to produce the aryl carbon-nitrogen bonds, e.g., to give a product such as 4-(4-(trifluoromethyl)phenyl)morpholine. In certain embodiments, the amine may be present in a molar excess to the aryl halide. In certain embodiments, the Ni salt catalyst solution includes a Ni(II) salt and a polar solvent, wherein the Ni(II) salt is dissolved in the polar solvent. In certain embodiments, the reactions conditions include holding the reaction mixture at between about room temperature and about 80° C. for between about 1 hour and about 20 hours such that at least about 50% yield is obtained.

23 Claims, 18 Drawing Sheets

(51) Int. Cl.
| | |
|---|---|
| *C07D 211/46* | (2006.01) |
| *C07C 209/68* | (2006.01) |
| *C07D 307/52* | (2006.01) |
| *C07D 213/74* | (2006.01) |
| *C07D 213/38* | (2006.01) |
| *C07D 239/26* | (2006.01) |
| *C07D 235/26* | (2006.01) |
| *B01J 19/12* | (2006.01) |
| *B01J 27/08* | (2006.01) |
| *B01J 35/00* | (2006.01) |
| *C07D 211/06* | (2006.01) |

(52) U.S. Cl.
CPC .......... *B01J 35/004* (2013.01); *C07C 209/68* (2013.01); *C07D 211/06* (2013.01); *C07D 211/46* (2013.01); *C07D 211/62* (2013.01); *C07D 213/38* (2013.01); *C07D 213/74* (2013.01); *C07D 235/26* (2013.01); *C07D 239/26* (2013.01); *C07D 307/52* (2013.01); *B01J 2219/0877* (2013.01); *B01J 2219/0892* (2013.01); *B01J 2219/1203* (2013.01); *C07C 2601/14* (2017.05)

(58) Field of Classification Search
CPC ... C07C 2601/14; B01J 19/123; B01J 19/127; B01J 2531/847; B01J 35/004; C07D 211/06; C07D 211/46; C07D 211/62; C07D 213/38; C07D 213/74; C07D 235/26; C07D 239/26; C07D 295/073; C07D 307/52
See application file for complete search history.

(56) References Cited

OTHER PUBLICATIONS

Li et al. (Angew., Chem. Int. Ed. 2017, 56, 13088-13093 and Supporting Information).*

Corcoran EB et al. Aryl amination using ligand-free Ni(II) salts and Photoredox catalysis. Science, vol. 353, Issue 6296, Jul. 15, 2016, pp. 279-283.

International Search Report and Written Opinion, PCT/US2019/030885, dated Apr. 21, 2020.

International Search Report and Written Opinion, PCT/US2019/061116, dated Jun. 10, 2020.

* cited by examiner

METHODS FOR FORMING ARYL CARBON-NITROGEN BOND USING LIGHT

CROSS-REFERENCE TO RELATED APPLICATIONS

The present application incorporates in its entirety and claims the benefit under 35 U.S.C. § 119(e) of U.S. Provisional Application No. 62/668,515 filed May 8, 2018, the contents of which is hereby incorporated by reference in its entirety.

GOVERNMENTAL RIGHTS

This invention was made with government support under F32GM122392 and R35GM119702 awarded by the National Institutes of Health and DE-AR0000881 awarded by the Defense Advanced Research Projects Agency. The government has certain rights in the inventions disclosed.

FIELD OF THE INVENTION

The present disclosure relates to methods for forming aryl carbon-nitrogen bonds and to photoreactors useful for conducting these and other light-driven reactions.

BACKGROUND OF THE INVENTION

C—N cross-coupling is an important class of reactions with far-reaching impacts across chemistry, materials science, biology, and medicine. Transition metal complexes can elegantly orchestrate diverse assemblies of aminations, however they typically require harsh reaction conditions, precious metal catalysts, or oxygen sensitive procedures.

What is needed, therefore, is a method for forming aryl carbon-nitrogen bonds that form under less extreme conditions and utilize an environmentally friendly catalyst.

Photochemistry comprises chemical reactions of atoms or molecules that have been electronically excited by absorption of light with wavelength typically in the range of 200 nm to about 700 nm. However, photoreactors used in connection with such photoreaction are often inefficient.

What is needed, therefore, are improved photoreactors for use in connection with photoreactions.

SUMMARY OF THE INVENTION

One aspect of the present disclosure is directed to a method for forming an aryl carbon-nitrogen bond. In certain embodiments, the method comprises contacting an aryl halide with an amine in the presence of a Ni salt catalyst solution and an optional base, thereby forming a reaction mixture, and exposing the reaction mixture to light under reaction conditions sufficient to form the aryl carbon-nitrogen bond.

In certain embodiments, the amine may be present in a molar excess to the aryl halide.

In certain embodiments, the Ni salt may be a nickel bromide salt such as $NiBr_2 \cdot 3H_2O$ salt.

In certain embodiments, the optional base may be an amine containing base such as quinuclidine.

In certain embodiments, the Ni salt catalyst solution includes a polar solvent, where the Ni salt is in the polar solvent. In other embodiments, the reaction mixture includes a polar solvent. In certain embodiments, the polar solvent may be N,N-dimethylacetamide.

In certain embodiments, the light may be visible light or UV light, e.g., 365 nm or 405 nm.

Another aspect of the present disclosure is directed to a method for forming aryl carbon-nitrogen bonds. The method comprising contacting an aryl halide with an amine in the presence of a $NiBr_2 \cdot 3H_2O$ salt, quinuclidine, and N,N-dimethylacetamide, thereby forming a reaction mixture, and exposing the reaction mixture to light at 365 nm under reaction conditions sufficient to form the aryl carbon-nitrogen bond.

Another aspect of the disclosure is directed to a photoreactor for performing a light-driven chemical reaction, the photoreactor comprising (1) a reaction chamber; (2) a modular reaction vial holder configured to hold one or more reaction vials located within the interior of the reaction chamber; (3) an LED Module comprising one or more LEDs that interfaces with the reaction chamber to provide light at desired wavelength(s) to the interior of the reaction chamber, a heatsink to extract heat from the one or more LEDs, and a first cooling source to cool the heatsink; and (4) a second cooling source to cool the reaction chamber.

In certain embodiments, the one or more LEDs are mounted to a metal core printed circuit board (MCPCB).

In other embodiments, the modular reaction vial holder is removable and replaceable.

In yet other embodiments, the reaction chamber may comprise a inner reflective surface coating.

These and other aspects and iterations of the disclosure are described in more detail below.

BRIEF DESCRIPTION OF THE FIGURES

(FIG. 12A) Light-driven C—S and C—N cross-couplings to construct molecular complexity. For the synthesis of 37, 1.0 equivalent of 4'-bromoacetophenone and 1.5 equivalent of 3-bromothiophenol were used; for the synthesis of 38, 1.5 equivalent of 3-aminopyridine and 1.5 equivalent of quinuclidine base were used. (FIG. 12B) Synthesis of flibanserin and two structurally related derivatives.

(FIG. 13A) UV-vis spectra of $NiBr_2 \cdot 3H_2O$ (A') and $NiBr_2 \cdot 3H_2O$+morpholine (A) in DMAc; 70 equivalent of morpholine was added with respect to $NiBr_2 \cdot 3H_2O$ in accordance to our standard reaction conditions; photographs showing the teal color of $NiBr_2 \cdot 3H_2O$ solution in DMAc was transformed to brownish yellow upon morpholine addition. (FIG. 13B) Proposed C—N cross-coupling mechanism derived from density functional theory (DFT) calculations. Reported free energies (in kcal/mol at 298 K and 1 M in solution) were computed at uM06/6-311+G(d,p)//uM06/6-31+G(d,p) level of theory with CPCM-described solvation in DMAc solvent. (FIG. 13C) Computed transition state structures for steps DE and DF. $\lambda_{max}$: maximum absorption wavelength; $\varepsilon_{max}$: molar absorptivity at $\lambda_{max}$; CPCM: conductor-like polarizable continuum model.

DETAILED DESCRIPTION OF THE INVENTION

Provided herein are methods for forming aryl carbon-nitrogen bonds. Suitable reaction components and parameters for forming aryl carbon-nitrogen bonds are detailed below. In accordance with certain aspects, the present disclosure provides a nickel-catalyzed C—N cross-coupling methodology that operates at room temperature using an inexpensive nickel source (e.g., a Ni bromide salt). In other aspects, the reaction is tolerant to oxygen and proceeds through direct irradiation of the Ni complex.

Certain aspects of the disclosure encompass a method for forming an aryl carbon-nitrogen bond. The method comprises contacting an aryl halide with an amine in the presence of a Ni salt catalyst solution and an optional base, thereby forming a reaction mixture, and exposing the reaction mixture to light under reaction conditions sufficient to produce the aryl carbon-nitrogen bond.

In certain embodiments, the light is visible light or UV light. In certain embodiments, the amine is present in a molar excess to the aryl halide. In certain embodiments, the Ni salt catalyst solution includes a Ni salt and a polar solvent, wherein the Ni salt is dissolved in the polar solvent. In other embodiments, the reaction mixture includes a polar solvent.

In certain embodiments, the reactions conditions include holding the reaction mixture at suitable temperatures, e.g., between about room temperature and about 100° C., between room temperature and about 90° C., between about room temperature and about 80° C., etc., for between about 30 minutes and about 20 hours, for between about 1 hour and about 20 hours, etc., such that at least about 50% yield, at least about 55% yield, at least about 60% yield, etc. is obtained.

Figure 1:
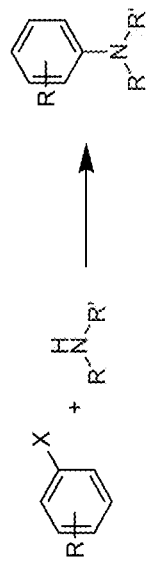
FIG. 1 depicts comparative highlights of historical C—N cross-coupling reactions and C—N cross-coupling reactions of the disclosure: T: temperature; rt: room temperature; UV: ultraviolet; PC: photoredox catalyst; LED: light-emitting diode

Aryl carbon-nitrogen (C—N) bonds are ubiquitous across a wide range of natural products and medicinally-relevant compounds,[1,2] making aminations one of the most important and frequently used reactions in medicinal chemistry.[3] Discovered in the early 1900s, copper-catalyzed Ullmann condensations constitute one of the oldest methods to construct an aryl C—N bond, however commonly require elevated temperatures that can limit reaction scope.[4,5] The field of transition metal catalyzed C—N bond formation has since evolved to provide a plethora of approaches for efficient aminations (FIG. 1). For example, palladium-catalyzed Buchwald-Hartwig C—N cross-coupling has become the predominant method for constructing aryl C—N bonds.[2,6,7] However, the use of palladium as well as the requirements for high temperatures (e.g., 80° C. or more) and strong alkoxide bases (e.g., $NaO^tBu$) presents toxicity concerns and can limit functional group tolerance. As such, the potential to use abundant nickel[8] in place of palladium has received significant interest.[9-11] The widespread use of the Ni(0) system is, however, hampered by the required use of high temperatures, strong alkoxide bases, and air-sensitive Ni(0) compounds (e.g., bis(cyclooctadiene)nickel),[12] and although methods that implement air-stable Ni(II) complexes have been developed, they do not address all of the challenges.

In recent years a new paradigm has arisen in aryl C—N bond formations that are driven by light or electricity in preference to heat. In 2012, a photoinduced Ullmann C—N cross-coupling was reported.[13] Deprotonated amine (e.g., carbazolide) and Cu(I) species form a Cu-amine complex (e.g., Cu-carbazolide complex). Upon light irradiation the Cu-amine complex and an aryl halide participated in a single electron transfer event to facilitate aryl C—N bond formation at room temperature.[14] This reaction, nevertheless, typically requires a strong alkoxide base, high energy UV irradiation (e.g., 254 nm), and has a restricted substrate scope. In 2016, dual photoredox systems driven by light and Ni catalysis for C—N cross-couplings were reported.[15,16] A Ni(II) salt (e.g., $NiBr_2$.glyme), in conjunction with an iridium-based photoredox catalyst (PC) proved successful in constructing aryl C—N bonds under blue LED irradiation and mild conditions (e.g., ligand-free, room temperature, and a mild organic base). In an ensuing report, it was demonstrated that dihydrophenazine[17] and phenoxazine[18] organic PCs as sustainable replacements for the precious metal iridium PC, achieving dual Ni/photoredox catalysis for aryl C—N bond formation under similar mild reaction conditions.[19] In addition to light, electricity was recently employed to alter the redox state of Ni to achieve aryl C—N bond formation, although electrochemical aryl amination involving anilines has not yet been demonstrated and the use of ligands is required.[20] Overall, mild and oxygen tolerant C—N bond forming reactions not requiring precious metals are still in need to be developed for this important chemical transformation.

In certain aspects, the present disclosure provides a light-driven, Ni-catalyzed C—N cross-coupling methodology that does not use an added photoredox catalyst and operates via direct photoexcitation of a reaction mixture. Without intending to be bound by theory, the present disclosure provides that the catalytically active Ni state for C—N cross-coupling can be accessed through an electronically excited nickel-amine complex without the aid of a supplementary photoredox catalyst to affect electron or energy transfer.[21,22]

Figure 2:
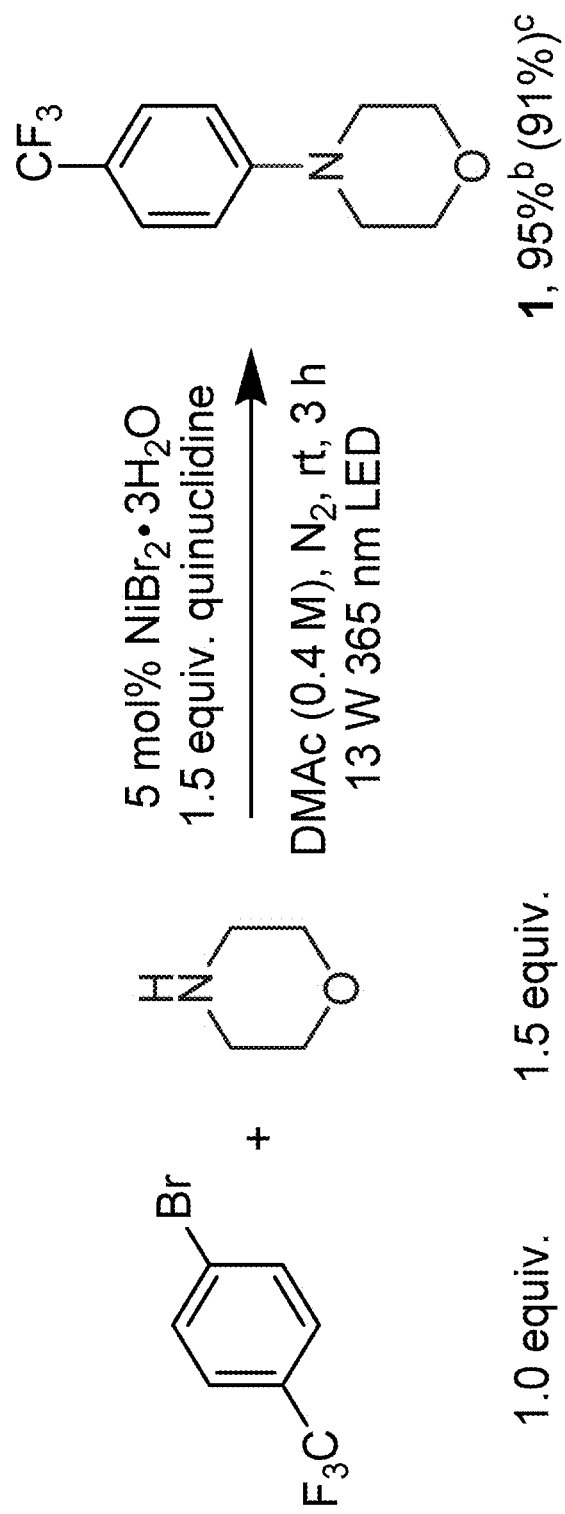
FIG. 2 depicts an exemplary C—N cross-coupling reaction of the disclosure.

In accordance with certain aspects of the disclosure, as described in the Examples below, it has been determined that efficient C—N cross-coupling at high yields can be achieved between an aryl halide (e.g., 4-bromobenzotrifluoride) and an amine (e.g., morpholine) when irradiated with ultraviolet LED (e.g., 365 nm) in the presence of a Ni(II) salt catalyst solution (e.g., a Ni DMAc solution containing 5 mol % $NiBr_2 \cdot 3H_2O$ and 1.5 equivalent quinuclidine) under a nitrogen atmosphere at room temperature (Table 1, FIG. 2). After 3 hours of irradiation, C—N coupled product 1 (FIG. 2) was obtained in 95% yield (determined from $^{19}$F-NMR), and was isolated at 91% yield. Control experiments revealed that no reaction occurred in the absence of light at either room temperature or 80° C. (Table 1, entry 1). Irradiation using a visible light 405 nm LED was similarly effective at promoting aryl C—N bond formation (93%, Table 1, entry 2) although proceeding at a slower rate. The nickel salt is crucial for amination as no reaction was observed in its absence (Table 1, entry 3). At 95% yield, both hydrated nickel salts $NiBr_2 \cdot 3H_2O$ and $NiCl_2 \cdot 6H_2O$ (Table 1, entry 5) gave identical yield to $NiBr_2 \cdot glyme$ (Table 1, entry 4), which was used in previous light or electrochemically driven C—N cross-coupling reactions (FIG. 1, schemes e, f, and g).[15,16,19,20] Markedly, hydrated nickel salts are at least two orders of magnitude cheaper than $NiBr_2 \cdot glyme$, thus rendering the aryl C—N cross-coupling methodology of the disclosure economically attractive.

TABLE 1

Reaction development and control experiments.[a]

| Entry | Deviation from conditions above | Yield[b] |
|---|---|---|
| 1 | No light (rt or 80° C.) | 0% |
| 2 | 13 W 405 nm LED | 93% |
| 3 | No nickel salt | 0% |
| 4 | 5 mol % $NiBr_2 \cdot glyme$ | 95% |
| 5 | 5 mol % $NiCl_2 \cdot 6H_2O$ | 95% |
| 6 | No quinuclidine base | 55% |
| 7 | No quinuclidine, 3.5 equiv. morpholine | 94% (87%)[c] |
| 8 | 1.5 equiv. DBU base | 2% |
| 9 | Same as entry 7 with presence of oxygen[d] | 91% |
| 10 | 1 hour | 72% |

[a]0.4 mmol scale; DMAc: N,N-dimethylacetamide; rt: room temperature; LED: light-emitting diode; DBU: 1,8-diazabicyclo[5.4.0]undec-7-ene.
[b]Yield determined by $^{19}$F-NMR.
[c]Isolated yield.
[d]Deoxygenasparged reaction mixture with air for two minutes prior to light irradiation.

(I) Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

(II) Methods

Certain aspects of the disclosure encompass a method for forming aryl carbon-nitrogen bonds. The method comprises contacting an aryl halide with an amine in the presence of a Ni salt catalyst solution and an optional base, thereby forming a reaction mixture; exposing the reaction mixture to a UV light under reaction condition sufficient to produce the aryl carbon-nitrogen bonds.

Another aspect of the present disclosure is directed to a method for forming aryl carbon-nitrogen bonds. The method comprising contacting an aryl halide with an amine in the presence of a Ni(II) salt, quinuclidine, and N,N-dimethylacetamide, thereby forming a reaction mixture, and exposing the reaction mixture to UV light under reaction conditions sufficient to form the aryl carbon-nitrogen bond.

In certain embodiments, the amine may be present in a molar excess to the aryl halide. In certain embodiments, the Ni salt catalyst solution includes a Ni(II) salt and a polar solvent, wherein the Ni(II) salt is dissolved in the polar solvent. In other embodiments, the reaction mixture may include a polar solvent. In certain embodiments, the reactions conditions include holding the reaction mixture at between about room temperature and about 80° C. for between about 1 hour and about 20 hours such that at least about 50% yield is obtained.

In other aspects, the method comprises contacting an aryl halide with an amine in the presence of a Ni(II) salt, a base, and a polar solvent, thereby forming a reaction mixture, and exposing the reaction mixture a UV light under reaction condition sufficient to produce the aryl carbon-nitrogen bonds.

In certain embodiments, the reactions conditions may be those described herein, e.g., holding the reaction mixture at between about room temperature and about 100° C., between room temperature and about 90° C., between about room temperature and about 80° C., etc., for between about 30 minutes and about 20 hours, for between about 1 hour and about 20 hours, etc., such that at least about 50% yield, at least about 55% yield, at least about 60% yield, etc. is obtained.

In certain aspects, the present disclosure provides a light-driven and nickel-catalyzed C—N cross-coupling methodology that proceeds via direct photoexcitation of a nickel-amine complex. Again, without intending to be limited by theory, the catalytically active nickel states can be efficiently accessed without requiring energy or electron transfer mechanisms from a supplemental photoredox catalyst. Secondary, primary alkyl, and primary (hetero)aryl amines can be effectively coupled to aryl halides with diverse electronics (see Examples) at room temperature without added ligand and, in many cases, without added base. The use of inexpensive hydrated nickel salts (e.g., $NiBr_2 \cdot 3H_2O$) in preference to considerably more expensive $NiBr_2 \cdot glyme$ significantly lowers the cost of this C—N cross-coupling methodology of the disclosure. The effectiveness of the methodology of the disclosure is highlighted by the successive use of light-driven C—S/C—N cross-couplings to synthesize complex structures as well as the synthesis of flibanserin and structurally related derivatives, discussed further herein.

Figure 3A:
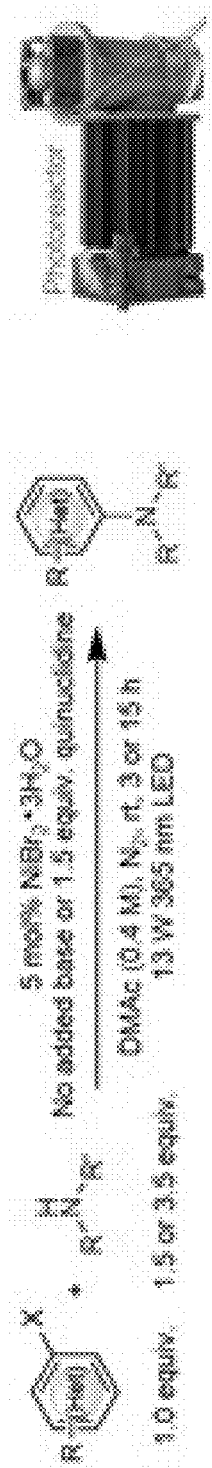
FIG. 3A, FIG. 3B, and FIG. 3C describe an exemplary C—N cross-coupling via direct photoexcitation of nickel-amine complex (FIG. 3A): amine (FIG. 3B) and aryl halide scope (FIG. 3C) in accordance with embodiments of the disclosure.
Figure 3B:
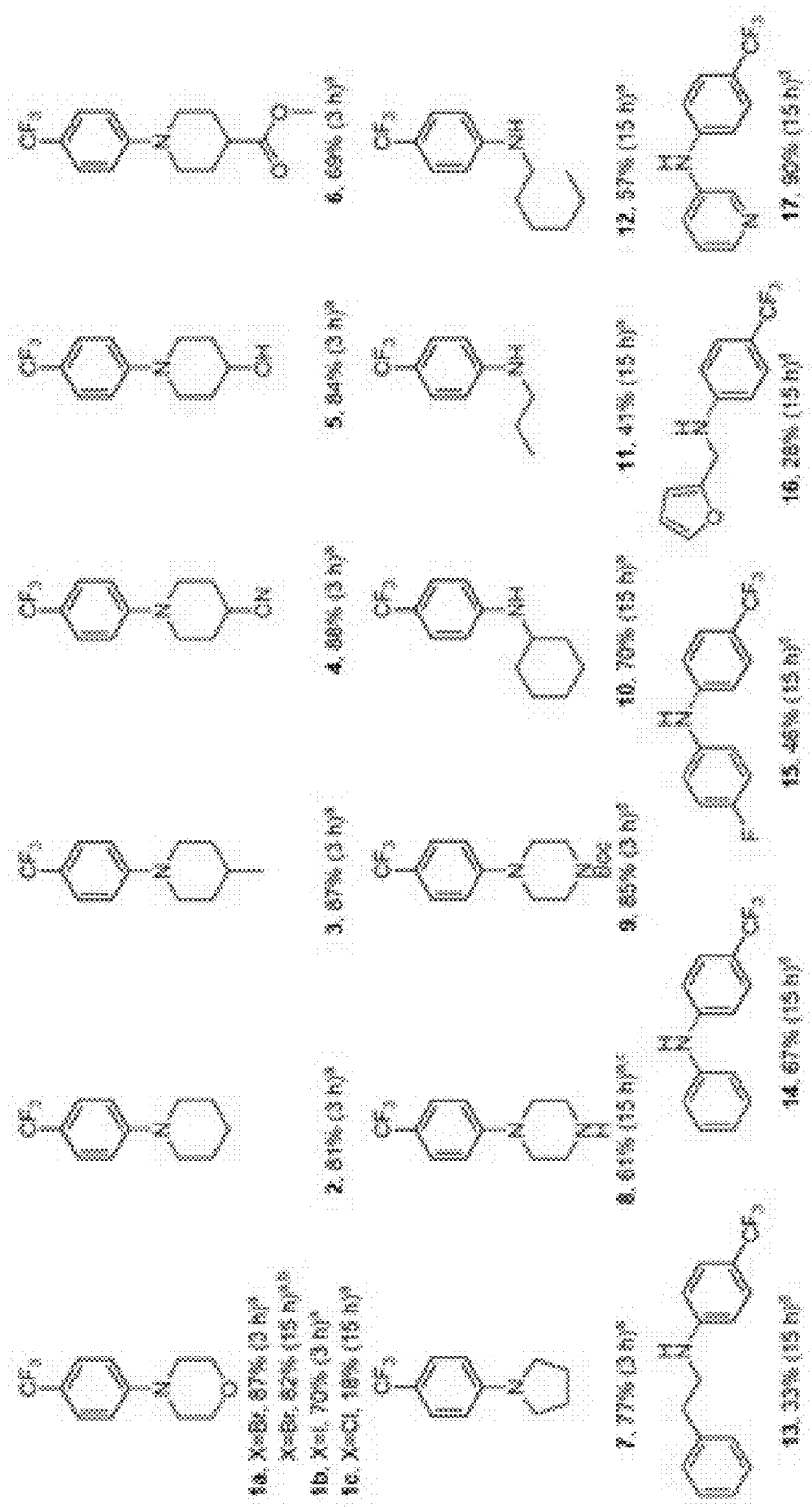
Figure 3C:
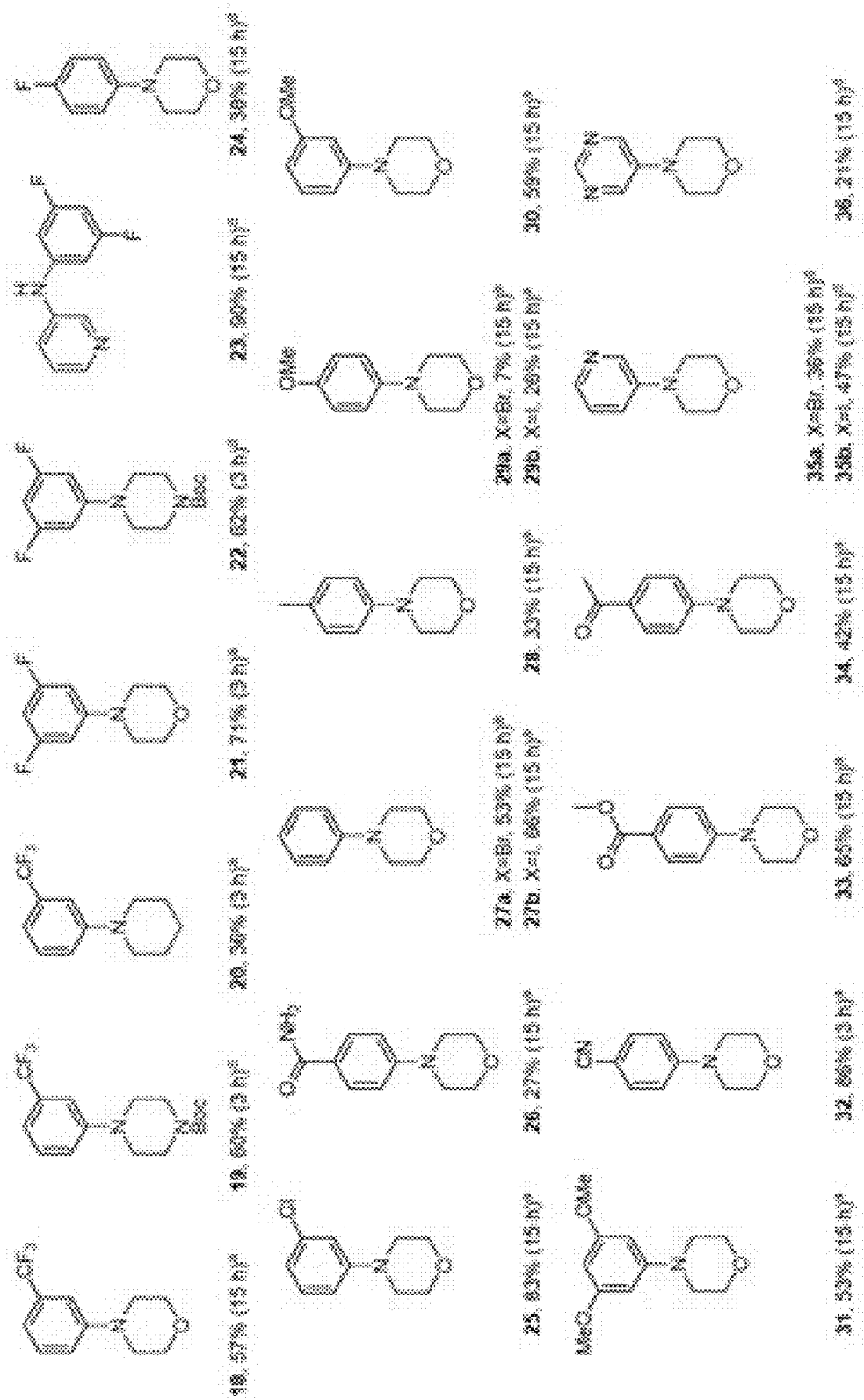

The application of this reaction methodology to various aryl halide, amine, and nickel salt catalyst solutions was investigated, as described herein. An exemplary C—N cross-coupling via direct photoexcitation of nickel-amine complex of the disclosure is illustrated in FIG. 3A, including a depiction of an exemplary photoreactor equipped with a 365 nm LED as described herein (DMAc: N,N-dimethylacetamide; rt: room temperature; LED: light-emitting diode; Boc: tert-butyloxycarbonyl. a 3.5 equiv. amine used with no added base. b 6.4 mmol scale reaction. c Dimethyl sulfoxide (DMSO) used as solvent. d 1.5 equiv. amine used with 1.5 equiv. quinuclidine base.) In FIG. 3B and FIG. 3C discussed below, unless otherwise specified, reactions were generally conducted at 0.4 mmol scale and aryl bromide was used as the coupling partner. Percent isolated yield are reported next to the product number (bolded).

(a) Aryl Halide

In general, the reaction comprises an aryl halide. In regards to the scope of aryl halides, the C—N cross-coupling methodology of the disclosure is compatible with any suitable aryl halide which provides sufficient reactivity to form the carbon-nitrogen bond. Without intending to be limited by theory, generally, aryl halides containing electron-withdrawing groups are more reactive than their electron-neutral or electron-donating counterparts. For example, when comparing substituents in the para position of an aryl bromide under similar reaction conditions, the yield of cyano (FIG. 3C, species 32, 86%) >hydrogen (FIG. 3C, species 27a, 53%) >methoxy (FIG. 3C, species 29a, 7%). The use of aryl iodides such as iodobenzene (FIG. 3C, species 27b, 66%), 4-iodoanisole (FIG. 3C, species 29b, 26%), and 3-iodopyridine (FIG. 3C, species 35b, 47%), resulted in increased yields relative to using aryl bromides.

In certain embodiments, the aryl halide may include trifluoromethyl (FIG. 3B, species 1-20), fluoro (FIG. 3C, species 21-24), chloro (FIG. 3C, species 25), amide (FIG. 3C, species 26), methyl (FIG. 3C, species 28), methoxy (FIG. 3C, species 29-31), cyano (FIG. 3C, species 32), ester (FIG. 3C, species 33), and carbonyl (FIG. 3C, species 34) functional groups. In other embodiments, the aryl halide may include heteroaryl halides including pyridine (FIG. 3C, species 35) and pyrimidine (FIG. 3C, species 36).

In accordance with aspects of the disclosure, the aryl halide may be an aryl bromide, an aryl chloride, or an aryl iodide. By way of example, suitable aryl halides include, without limit, aryl bromide (e.g., bromobenzene; 4-bromobenzotrifluoride; 3-bromobenzotrifluoride; 1-bromo-3,5-diflurobenzene; 4-bromobenzofluoride; 1-bromo-3-(trifluoromethyl)benzene; 1-bromo-3-chlorobenzene; 4-bromobenzamide; 1-bromo-4-methylbenzene; 1-bromo-4-methoxybenzene; 1-bromo-3-methoxybenzene; 1-bromo-3,5-dimethoxybenzene; 4-bromobenzonitrile; methyl 4-bromobenzoate; 1-(4-bromophenyl)ethan-1-one; 3-bromopyridine; 5-bromopyrimidine, and the like), aryl chloride (e.g., chlorobenzene; 4-chlorobenzotrifluoride; 3-chlorobenzotrifluoride; 1-chloro-3,5-diflurobenzene; 4-chlorobenzofluoride; 1-chloro-3-(trifluoromethyl)benzene; 1-chloro-3-chlorobenzene; 4-chlorobenzamide; 1-chloro-4-methylbenzene; 1-chloro-4-methoxybenzene; 1-chloro-3-methoxybenzene; 1-chloro-3,5-dimethoxybenzene; 4-chlorobenzonitrile; methyl 4-chlorobenzoate; 1-(4-chlorophenyl)ethan-1-one; 3-chloropyridine; 5-chloropyrimidine, and the like), and aryl iodide (e.g., iodobenzene; 4-iodobenoztrifluoride; 3-iodobenzotrifluoride; 1-iodo-3,5-diflurobenzene; 4-iodobenzofluoride; 1-iodo-3-(trifluoromethyl)benzene; 1-iodo-3-chlorobenzene; 4-iodobenzamide; 1-iodo-4-methylbenzene; 1-iodo-4-methoxybenzene; 1-iodo-3-methoxybenzene; 1-iodo-3,5-dimethoxybenzene; 4-iodobenzonitrile; methyl 4-iodobenzoate; 1-(4-bromophenyl)ethan-1-one; 3-iodopyridine; 5-iodopyrimidine, and the like).

(b) Amine

In another aspect of the disclosure, the reaction comprises an amine. In some embodiments, the amine may be a primary amine or secondary amine. In other embodiments, the amine may be a secondary amine.

In accordance with the disclosure, the impact of the amine was investigated (FIG. 3B). Secondary (FIG. 3B, species 1-9), primary alkyl (FIG. 3B, species 10-13) and primary (hetero)aryl amines (FIG. 3B, species 14-17) were all successfully coupled with an aryl halide (e.g., 4-bromobenzotrifluoride) to yield the corresponding C—N products.

By way of non-limiting example, for morpholine, in addition to aryl bromide (FIG. 3B, species 1a, 87%), 4-iodobenzotrifluoride (FIG. 3B, species 1b) was effectively coupled in 70% isolated yield in 3 hours. 4-chlorobenzotrifluoride (FIG. 3B, species 1c), in contrast, gave 18% yield after 15 hours of irradiation. C—N cross-coupling between morpholine and 4-bromobenzotrifluoride was further scaled to 6.4 mmol and isolated in 82% yield (1.21 grams) after 15 hours of irradiation. Piperidine (FIG. 3B, species 2, 81%) and pyrrolidine (FIG. 3B, species 7, 77%) were both coupled in high yield without added base. A variety of functional groups were tolerated under these reaction conditions. For example, piperidine derivatives containing methyl (FIG. 3B, species 3, 87%), cyano (FIG. 3B, species 4, 88%), hydroxyl (FIG. 3B, species 5, 84%), and ester (FIG. 3B, species 6, 69%) functional groups were efficiently coupled. Highlighting the tolerance to oxygen, species 3 was isolated in 86% yield when the solvent and reagents were used as received, without degassing. Significantly, hydroxyl groups are tolerated by this C—N coupling condition as a strong base (e.g., alkoxide) is not employed. The efficacious coupling of unprotected piperazine (FIG. 3B, species 8, 61%) is particularly notable as the aryl C—N coupled piperazine moiety is prevalent among therapeutic compounds[28] such as aripiprazole and flibanserin, although the Boc-protected piperazine (FIG. 3B, species 9) was shown to be more reactive, yielding the C—N product in 85%.

In accordance with certain aspects of the disclosure, primary alkyl amines were typically less reactive than secondary amines, generally resulting in lower yield while requiring longer irradiation times (e.g., 15 hours). Nonetheless, cyclohexylamine (FIG. 3B, species 10, 70%), propylamine (FIG. 3B, species 11, 41%), hexylamine (FIG. 3B, species 12, 57%), and phenethylamine (FIG. 3B, species 13, 33%) were successfully coupled to an aryl halide (e.g., 4-bromobenzotrifluoride) in moderate to good yield. It is noteworthy that phenethylamine and its analogues are naturally-occurring alkaloids that are commonly found in psychoactive drugs.[29] Furfuryl amine (FIG. 3B, species 16, 28%) and aromatic amines such as aniline (FIG. 3B, species 14, 67%), 4-fluoroaniline (FIG. 3B, species 15, 46%), and 3-aminopyridine (FIG. 3B, species 17, 90%) were also effectively coupled. Since aromatic amines are less basic than primary or secondary alkyl amines, 1.5 equivalent of quinuclidine as the base was required to obtain appreciable yields.

Suitable primary amines include, without limit, propylamine, cyclohexylamine, phenethylamine, pyridine-3-amine, furan-2-ylmethanamine, aniline, 4-fluoroaniline, and pyrrolidine.

Suitable secondary amines include, without limit, piperidine, morpholine, 4-methyl-piperidine, piperdine-4-ol, piperidine-4-carbonitrile, methyl piperidine-4-carboxylate, cyclohexanamine, 3-aminopyridine, propan-1-amine, hexan-1-amine, and 2-phenylethan-1-amine.

In some embodiments, the amine in the reaction mixture may generally be present in a molar excess to the aryl halide. In certain embodiments, the amine may be present from about 1.1 to about 5.5 equivalents, from about 1.1 to about 4.5, from about 1.1 to about 3.5, etc., to 1 equivalent of the aryl halide. In some embodiments, the amine in the reaction mixture may be about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.7, about 2.8, about 2.9, about 3.0, about 3.1, about 3.2, about 3.3, about 3.4, about 3.5, about 3.6, about 3.7, about 3.8, about 3.9, about 4.0 equivalents, etc., of the aryl halide. In an exemplary embodiment, the amine in the reaction mixture may be present from about 1.5 equivalents to about 3.5 equivalents to 1 equivalent of the aryl halide.

(c) Nickel (Ni) Salt Catalyst Solution

In general, the reaction is performed in the presence of a nickel salt catalyst solution. In some embodiments, the nickel salt catalyst solution may include a nickel salt and a solvent, e.g., a polar solvent, which the nickel salt is dissolved in. In some embodiments, the nickel may have an oxidation number of +2 (i.e., Ni(II)).

Any suitable nickel salt may be used in connection with the methods of the disclosure, preferably those with an oxidation number of +2 (i.e., Ni(II)). Exemplary nickel salts include, without limit, a nickel bromide salt (e.g., $NiBr_2$.glyme, $NiBr_2.3H_2O$, and the like), a nickel chloride salt (e.g., $NiCl_2.6H_2O$, $NiCl_2$.glyme, and the like), a nickel fluoride salt, a nickel iodide salt, a nickel carbonate salt, a nickel perchlorate salt, a nickel sulfamate salt, a nickel sulfate salt, etc. In an exemplary embodiment, the nickel salt may be $NiBr_2.3H_2O$. By way of non-limiting example, suitable nickel salts include Ammonium nickel(II) sulfate hexahydrate, Nickel(II) acetate tetrahydrate, Nickel(II) bromide anhydrous, Nickel(II) bromide, Nickel(II) bromide hydrate, Nickel carbonate, basic hydrate, Nickel(II) carbonate hydroxide tetrahydrate, Nickel(II) chloride anhydrous, Nickel(II) chloride, Nickel(II) fluoride, Nickel(II) hydroxide, Nickel(II) iodide anhydrous, Nickel(II) iodide, Nickel (II) nitrate hexahydrate, Nickel(II) perchlorate hexahydrate, Nickel(II) sulfamate tetrahydrate, Nickel(II) sulfate anhydrous, and Nickel(II) sulfate heptahydrate. In other embodiments, suitable nickel salts include $NiBr_2$.glyme, $NiCl_2.6H_2O$, $NiCl_2$.glyme, and $NiBr_2.3H_2O$.

As discussed herein, in some embodiments, the nickel salt may be dissolved in a solvent, particularly a polar solvent. In other embodiments, the reaction mixture may include a polar solvent, and the components of the reaction mixture may be dissolved in the polar solvent. Suitable polar solvents include, without limit, N,N-dimethylacetamide (DMAc), dimethyl sulfoxide (DMSO), methanol (MeOH), dimethylformamide (DMF), acetonitrile (MeCN), and the like. In an exemplary embodiment, the polar solvent may be N,N-dimethylacetamide.

In some embodiments, the amount of nickel salt in the reaction mixture may be from about 1 mol % to about 15 mol %. In other embodiments, the amount of nickel salt in the reaction mixture may be about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, or about 15 mol %. In other embodiments, the nickel salt may be present in the reaction mixture in an amount ranging from about 0.01 equivalents to about 0.1 equivalents, about 0.01 equivalents to about 0.05 equivalents, about 0.05 equivalents, of the aryl halide.

(d) Base

In certain embodiments, the reaction may be carried out in the presence of an optional base. In certain embodiments, the base may be an amine containing base. Suitable bases include, without limit, quinuclidine, morpholine, N-methyl-morpholine, N,N-diisopropylethylamine (DIPEA), 1,4-diazabicyclo[2.2.2]octane (DABCO), 4-dimethylaminopyridine (DMAP), 1,8-diazabicyclo[5.4.0]undec-7-ene (DBU), N,N, N',N'',N''-pentamethyldiethylenetriamine (PMDTA), triethylamine (TEA), proton sponge, and the like. In an exemplary embodiment, the base may be quinuclidine.

In particular embodiments, the optional base may be selected from quinuclidine, morpholine, N-methyl-morpholine, triethylamine, N,N-diisopropylethylamine (DIPEA), and DABCO (1,4-diazabicyclo[2.2.2]octane). In another embodiment, the optional base may be selected from quinuclidine, morpholine, N-methyl-morpholine, triethylamine, and N,N-diisopropylethylamine (DIPEA). In another embodiment, the optional base may be selected from quinuclidine, morpholine, triethylamine, and N,N-diisopropylethylamine (DIPEA). In other embodiments, no base may be utilized, and instead a molar excess of amine may be used, as discussed further herein.

In accordance with aspects of the disclosure and described in the Examples below, the choice of base significantly impacts the yield of the reaction. In accordance with aspects of the disclosure, it has been unexpectedly found that quinuclidine outperforms other organic bases such as triethylamine, N,N-diisopropylethylamine and DABCO (1,4-diazabicyclo[2.2.2]octane), while the stronger base DBU (1,8-Diazabicyclo(5.4.0)undec-7-ene) almost completely halts the reaction (2% yield, Table 1, entry 8). Unexpectedly, 55% yield is obtained in the absence of a base (Table 1, entry 6), where excess morpholine acts to neutralize the HBr by-product. As such, in certain aspects of the disclosure, using a larger excess of morpholine (e.g., 3.5 equiv., Table 1, entry 7), the yield improves to 94% (87% isolated). In addition to water tolerance (through use of $NiBr_2.3H_2O$), the presence of oxygen also does not appreciably affect the yield (91%, Table 1, entry 9). Kinetically, this C—N cross-coupling reaction is reasonably fast, reaching 72% after one hour of irradiation (Table 1, entry 10).

In some embodiments, the base may be present in the reaction mixture in an amount ranging from about 0.5 to about 2.5 equivalents to 1 equivalent of the aryl halide. In some embodiments, the base in the reaction mixture may be about 1, about 1.1, about 1.2, about 1.3, about 1.4, about 1.5, about 1.6, about 1.7, about 1.8, about 1.9, about 2, about 2.1, about 2.2, about 2.3, about 2.4, or about 2.5 equivalents of the aryl halide. In an exemplary embodiment, the base in the reaction mixture may be present from about 1.5 equivalents to 1 equivalent of the aryl halide.

(e) Light

In general, the aryl C—N coupling reaction of the disclosure reaction is performed in the presence of light. In some embodiments, the light may be visible light or UV light.

In an embodiment, visible light may be from about 390 nm to about 700 nm. In other embodiments, visible light may be from about 390 nm to about 600 nm, about 390 nm to about 500 nm, or about 390 nm to about 400 nm. In an exemplary embodiment, the reaction is may be performed in the presence of visible light at about 405 nm.

In an embodiment, UV light may be from about 10 nm to about 400 nm. In other embodiments, UV light may be from about 100 nm to about 400 nm, about 200 nm to about 400 nm, about 300 nm to about 400 nm, about 350 nm to about 400 nm, about 365 nm to about 400 nm, etc. In an exemplary embodiment, the reaction may be performed in the presence of UV light at about 365 nm.

In other embodiments, the light may be from about 10 nm to about 1000 nm. In some embodiments, the light may be from about 100 nm to about 1000 nm, about 200 nm to about 1000 nm, about 300 nm to about 1000 nm, about 100 nm to about 900 nm, about 100 nm to about 800 nm, about 100 nm to about 700 nm, about 100 nm to about 600 nm, about 100 nm to about 500 nm, or about 100 nm to about 400 nm.

(f) Reaction Conditions and Yield

In some embodiments, the aryl C—N coupling reaction of the disclosure occurs for about 30 minutes to about 20 hours, about 1 hour to about 20 hours, about 1 hours to about 15 hours, about 1 hours to about 10 hours, about 1 hours to about 5 hours, about 1 hours to about 4 hours, about 1 hours to about 3 hours, etc. In other embodiments, the reaction occurs for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, or about 20 hours. In yet other embodiments, the reaction occurs for at least about 1 hour, at least about 2 hours, at least about 3 hours, at least about 4 hours, at least about 5 hours, etc.

In general, the aryl C—N coupling reaction of the disclosure may be performed at room temperature or at an elevated temperature. In some embodiments, the reaction may be performed at about 25° C., about 30° C., about 35° C., about 40° C., about 45° C., about 50° C., about 55° C., about 60° C., about 65° C., about 70° C., about 75° C., about 80° C., or about 85° C. In an exemplary embodiment, the reaction may be performed at about 25° C. (e.g., room temperature). In certain embodiments, the reaction may be performed at between about room temperature and about 100° C., between room temperature and about 90° C., between about room temperature and about 80° C., etc.

In general, the aryl C—N coupling reaction of the disclosure may be performed under an inert atmosphere. In some embodiments, the inert atmosphere may comprise nitrogen, helium, argon, krypton, xenon, and radon. In an exemplary embodiment, the inert atmosphere may comprise nitrogen.

In certain embodiments, the aryl C—N coupling reaction of the disclosure may be performed under reaction conditions sufficient to result in about 30% yield, at least about 35% yield, at least about 40% yield, at least about 45% yield, at least about 50% yield, at least about 55% yield, at least about 60% yield, at least about 65% yield, at least about 70% yield, at least about 75% yield, at least about 80% yield, at least about 85% yield, at least about 90% yield, at least about 93% yield, at least about 95% yield, at least about 97% yield, at least about 98% yield, etc.

In certain embodiments, the aryl C—N coupling reaction of the disclosure may be performed under reaction conditions sufficient to form aryl carbon-nitrogen bond(s). As described herein, such reactions conditions include, e.g., holding the reaction mixture at between about room temperature and about 100° C., between room temperature and about 90° C., between about room temperature and about 80° C., between about 25° C. and about 100° C., between about 25° C. and about 90° C., between about 25° C. and about 80° C., etc., for between about 30 minutes and about 20 hours, about 1 hour and about 20 hours, about 1 hour and about 15 hours, about 1 hour and about 10 hours, about 1 hour and about 5 hours, etc., such that at least about 50% yield, at least about 55% yield, at least about 60% yield, at least about 65% yield, at least about 70% yield, at least about 75% yield, at least about 80% yield, at least about 85% yield, at least about 90% yield, at least about 93% yield, at least about 95% yield, etc., is obtained.

The methods for forming aryl carbon-nitrogen bonds as described herein may be used to couple piperazine to aryl halides to produce precursors prevalent in many pharmaceutical active ingredients. By way of non-limiting example, the methods for forming aryl carbon-nitrogen bonds may be used to couple piperazine to 2,3-dichlorobromobenzene or 1,2-dichloro-3-iodobenzene to produce a C—N coupled precursor, which is used to produce AMBILIFY; to couple 2,6-dichloroaniline and 2-bromophenylacetic acid or 2-iodophenylacetic acid to produce DICLFENAC.

(III) Photoreactor

Figure 4:
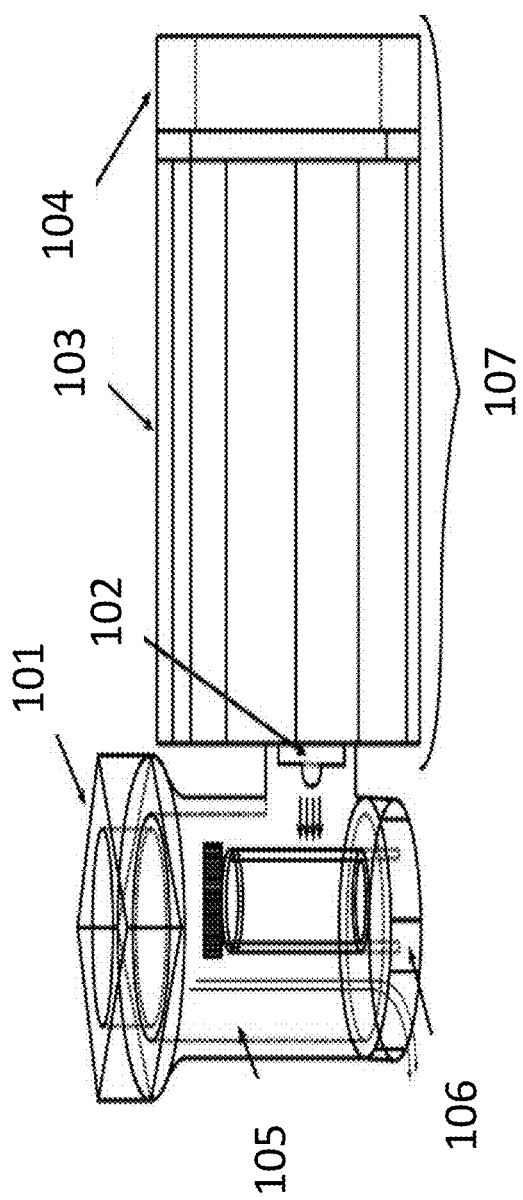
FIG. 4 depicts a schematic of a photoreactor of the disclosure.

This C—N coupling reaction utilizes a high radiant flux setup to achieve reduced reaction times. To this end, in another aspect of the disclosure, a photoreactor was developed (FIG. 4). However, it will be understood by those of skill in the art that the photoreactor of the disclosure is not limited to the C—N coupling reactions disclosed herein, and may be useful to perform any light-driven chemical reaction known in the art.

Now, with reference to FIG. 4, photoreactor 100 includes: (1) a reaction chamber 105; (2) a modular reaction vial holder 106 configured to hold one or more reaction vials located within the interior of the reaction chamber; (3) an LED Module 107 comprising one or more LEDs 102 that interfaces with the reaction chamber 105 to provide light at desired wavelength(s) to the interior of the reaction chamber, a heatsink 103 to extract heat from the one or more LEDs 102, and a first cooling source 104 to cool the heatsink 103; and (4) a second cooling source 101 to cool the reaction chamber.

The reaction chamber includes an interior wall and exterior wall so as to form an interior area. The modular reaction vial holder is located within the interior area of the reaction chamber. As described in further detail herein, the LED Module interfaces with the reaction chamber such that the one or more LEDs emit light into the interior area of the reaction chamber. For instance, in certain embodiments, there may be an opening perpendicular to the principal axis of the reaction chamber through which the LED emitter is oriented so that it irradiates the interior of the reaction chamber. Further, in certain embodiments, the interior wall of the reaction chamber may include a reflective surface coating, as described in further detail herein.

In certain embodiments, the one or more LEDs may be industrial light emitting diodes (LEDs) which provide high radiant flux at a desired wavelength, e.g., between 200 nm to 700 nm, specifically 365 nm or 405 nm for the C—N coupling reactions of the disclosure. In certain aspects of the disclosure, the LEDs produce enough heat that active cooling is needed both to protect the LED and to ensure that its emission profile remains constant throughout the reaction.

To facilitate this, in certain aspects of the disclosure, the LED Module may further include a metal core printed circuit board (MCPCB). In certain embodiments, the one or more LEDs may be mounted to the MCPCB, and the MCPCB may in turn be mounted to the heatsink. Again, with reference to FIG. 4, the one or more LEDs 102 may be mounted to a MCPCB to enable efficient heat transfer from the LEDs 102 to the heatsink 103. In accordance with the disclosure, any suitable heatsink may be used which is sufficient to absorb the emitted heat from the LEDs, e.g., an aluminum heatsink. This heatsink 103 is then actively cooled by a first cooling source 104, e.g., by a 60 mm computer fan. In addition, the reaction chamber may be separately cooled by a second cooling source 101, e.g., a 40 mm computer fan or water/fluid cooling jacket, to allow for consistent reaction conditions. However, any suitable method for cooling the LEDs and reaction chamber may be utilized without departing from the scope of the disclosure.

In certain embodiments, if desired, the reaction chamber 105 may include a reflective interior surface coating, e.g., formed from aluminum tape or similar reflective material, to maximize reflection of emitted light back to the reaction vial.

In certain embodiments, the photoreactor also includes a modular reaction vial holder 106 that ensures consistent vial placement and distance from the one or more LEDs 102, and allows for consistent irradiation and cooling of the reaction vial. In certain embodiments, the modular reaction vial holder 106 is removable and replaceable, with size and shape to accommodate the desired reaction vial size and volume. Further, the modular reaction vial holder 106 may be located within the reaction chamber 105 at any suitable location so as to achieve the desired reaction conditions.

By way of non-limiting example, in one embodiment, the vial may be sized to accommodate from about 0.1 mL to about 30 mL. In other embodiments, the vial may be sized to accommodate about 0.2 mL (0.5 dram), 0.6 mL (1.5 dram), or 20 mL. In one embodiment, the vial may be from about 1 mm to about 20 mm from the LED light. In other embodiments, the vial may be about 1 mm, about 5 mm, about 10 mm, about 15 mm, or about 20 mm from the LED light.

The LED Module 107 comprising the one or more LEDs 102, the heatsink 103, and the first cooling source 104 may be configured to allow for easy and facile exchange of LEDs with differing emission wavelengths, as may be desired.

The photoreactor may generally be constructed from commercially available parts, with the exception of the reaction chamber and modular reaction vial holder. In accordance with aspects of the disclosure, the reaction chamber and modular reaction vial holder may be sized and shaped as desired, and printed using a 3D-printer, or formed using any suitable methodology known in the art.

For instance, the modular reaction vial holder, reaction chamber body, and fan adapter parts were designed in-house using Autodesk Inventor software and 3D-printed using stereolithography with a Form2 printer (FormLabs) or fused filament fabrication with a Creator Pro (Flashforge). Modular reaction vial position in the reaction chamber was optimized by 3D-printing vial holders with distances of 5 mm, 10 mm, and 15 mm from the LED emitter surface to the vial. The 5 mm position yielded higher NMR conversion after 1 hour compared to other distances under standard reaction conditions on a 0.2 mmol scale (Table 2).

TABLE 2

The model reaction was performed on a 0.2 mmol scale (half scale compared to other reported reactions) with varying irradiation distances. In certain embodiments of the disclosure, at 0.4 mmol scale, 72% yield was achieved after 1 hour at 5 mm irradiation distance. Yields were determined by $^{19}$F NMR.

| Entry | Deviation from conditions above | Yield |
|---|---|---|
| 1 | 5 mm irradiation distance | 91% |
| 2 | 10 mm irradiation distance | 75% |
| 3 | 15 mm irradiation distance | 69% |

As constructed, the reaction chamber is cylindrical in shape and oriented vertically, with a computer fan screwed to the top that blows air downwards. However, other suitable sizes and configurations may be used, as recognized by those of skill in the art. As described herein, the interior wall of the reaction chamber may be coated with to provide a reflective finish to redirect light towards the center of the chamber. In certain embodiments, the reaction chamber may be configured to include an opening perpendicular to the principal axis of the reaction chamber through which the LED emitter is oriented so that it irradiates the center/interior of the chamber. The perpendicular opening may be sized and shaped so as to interface and mate with the LED emitter in a suitable manner, e.g., to minimize light loss to the surrounding environment.

In certain embodiments, the reaction vial holder may be 3-D printed so as to be modular with different versions sized to hold, e.g., 0.5 dram, 1.5 dram, or 20 mL scintillation vials. In certain embodiments, the modular reaction vial holder may be configured with an open design that maximizes airflow when attached to the reaction chamber. It may be designed to provide an optimized distance, e.g., of 5 mm, 10 mm, 15 mm, etc., from the vial edge to the LED emitter lens when the vial is held in place and the modular reaction vial holder is attached to the reaction chamber. The design may additionally be optimized to minimize blockage of incoming light from the LED. Alternatively, a version incorporating a heating/cooling jacket has also been developed that allows for direct heating or cooling of the reaction vial via a suitable coolant fluid, e.g., water, brine, ammonia, glycerol, ethylene glycol, etc., depending on the heat transfer required.

In certain embodiments, the LED Module including the LED-heatsink-fan assembly may be configured to be modular so that it can be easily switched between assemblies with different mounted LEDs (i.e. with different emitter wavelengths). LEDs are commercially available mounted to a MCPCB. This package may then mounted on one end of the heatsink (also commercially available) utilizing a thermally conducting paste (commercially available) and may be screwed in for security. A computer fan may be attached to the other end of the heatsink via a 3D-printed adapter.

In use, these components function to irradiate a vial with high-flux light while simultaneously cooling both the reaction chamber and the LED, thus enabling consistency and efficient temperature control. In addition, the design of the photoreactor of the disclosure allows for reaction vial volumes that range from 20 mL to less than 0.5 mL in scale. This enhanced flexibility provides for improved scope of use.

All reactions described in the examples herein were performed at the 5 mm irradiation distance.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Anhydrous DMAc solvent, aryl halides, and amines were purchased from Sigma-Aldrich (St. Louis, Mo.), TCI (Portland, Oreg.), or Alfa Aesar (Haverhill, Mass.). All commercially available solvents and reagents were degassed and used without further purifications. The photoreactor was custom designed and built. Organic solutions were concentrated under reduced pressure on a BÜCHI rotary evaporator (New Castle, Del.) using a water bath. Flash column chromatography was performed using the COMBIFLASH Rf+ Lumen instrument (Lincoln, Nebr.). Reactions were analyzed by TLC using TLC silica gel F254 250 μm precoated-plates from Merck (Kenilworth, N.J.). Developed chromatogram was visualized using a UV lamp and permanganate stain was used for UV-inactive compounds.

The $^1$H, $^{13}$C, and $^{19}$F NMR spectra were recorded on a Bruker Avance Neo (400, 101, and 376 MHz, respectively) instrument. Deuterated solvents were purchased from Cambridge Isotope Laboratories (Andover, Mass.) and used as received. All $^1$H NMR experiments are reported in δ units, parts per million (ppm), and were measured relative to the signals for residual chloroform (7.26 ppm) or dimethylsulfoxide (2.50 ppm) in the deuterated solvents. Data for $^1$H NMR are reported as follows: chemical shift (δ ppm), multiplicity (s=singlet, d=doublet, t=triplet, q=quartet, p=quintet, m=multiplet, dd=doublet of doublets, dt=doublet of triplets . . . etc, br=broad), coupling constant (Hz) and integration. All $^{13}$C NMR spectra are reported in ppm relative to CDCl$_3$ (77.16 ppm) or DMSO-d$_6$ (39.52 ppm). Mass spectrometry analysis was performed using an Agilent 6220 TOF LC/MS ("QTOF") interfaced to an Agilent 1200 HPLC with electrospray (ESI), multi-mode (combined ESI and APCI), atmospheric pressure photoionization (APPI), and Direct Analysis in Real Time (DART) sources at Colorado State University.

The following abbreviations are used in the Examples: CPCM: conductor-like polarizable continuum model; DFT: density functional theory; DMSO: dimethyl sulfoxide; Eq or equiv: equivalent; λmax: maximum absorption wavelength; and εmax: molar absorptivity at λmax.

Example 1. C—N Cross-Coupling Via Direct Photoexcitation of Nickel-Amine Complexes General Procedure A:

Under nitrogen atmosphere in a glovebox, a stir bar, an aryl halide (0.40 mmol, 1.0 equivalent), and 1 mL of DMAc solution containing dissolved NiBr$_2$.3H$_2$O (0.02 mmol, 0.05 equiv., 5.5 mg) was added to a 0.5 dram glass vial. The glass vial was then capped using a screw cap equipped with a PTFE/silicone septum and sealed with a strip of PARAFILM. The capped vial was then brought out of the glovebox and liquid amine (degassed, 1.40 mmol, 3.5 equiv.) was added via a HAMILTON syringe. Solid amines were weighed and added inside the glovebox. The capped glass vial containing the reaction mixture was then placed in a 3D-printed vial holder and subjected to 365 nm LED irradiation with fan cooling to maintain the vial at room temperature. After the time specified in the reaction schemes, the reaction mixture was washed with water, extracted with EtOAc or DCM and concentrated under vacuum. Purification of the crude product by flash chromatography on silica gel using the indicated solvent system afforded the desired product.

General Procedure B:

Under nitrogen atmosphere in a glovebox, a stir bar, an aryl halide (0.40 mmol, 1.0 equiv.), quinuclidine (0.60 mmol, 1.5 equiv., 66.7 mg), and 1 mL of DMAc solution containing dissolved NiBr$_2$.3H$_2$O (0.02 mmol, 0.05 equiv., 5.5 mg) was added to a 0.5 dram glass vial. The glass vial was then capped using a screw cap equipped with a PTFE/silicone septum and sealed with a strip of PARAFILM. The capped vial was then brought out of the glovebox and liquid amine (degassed, 0.60 mmol, 1.5 equiv.) was added via a HAMILTON syringe. Solid amines were weighed and added inside the glovebox. The capped glass vial containing the reaction mixture was then placed in a 3D-printed vial holder and subjected to 365 nm LED irradiation with fan cooling to maintain the vial at room temperature. After the time specified in the reaction schemes, the reaction mixture was washed with water, extracted with EtOAc or DCM and concentrated under vacuum. Purification of the crude product by flash chromatography on silica gel using the indicated solvent system afforded the desired product.

Figure 5:
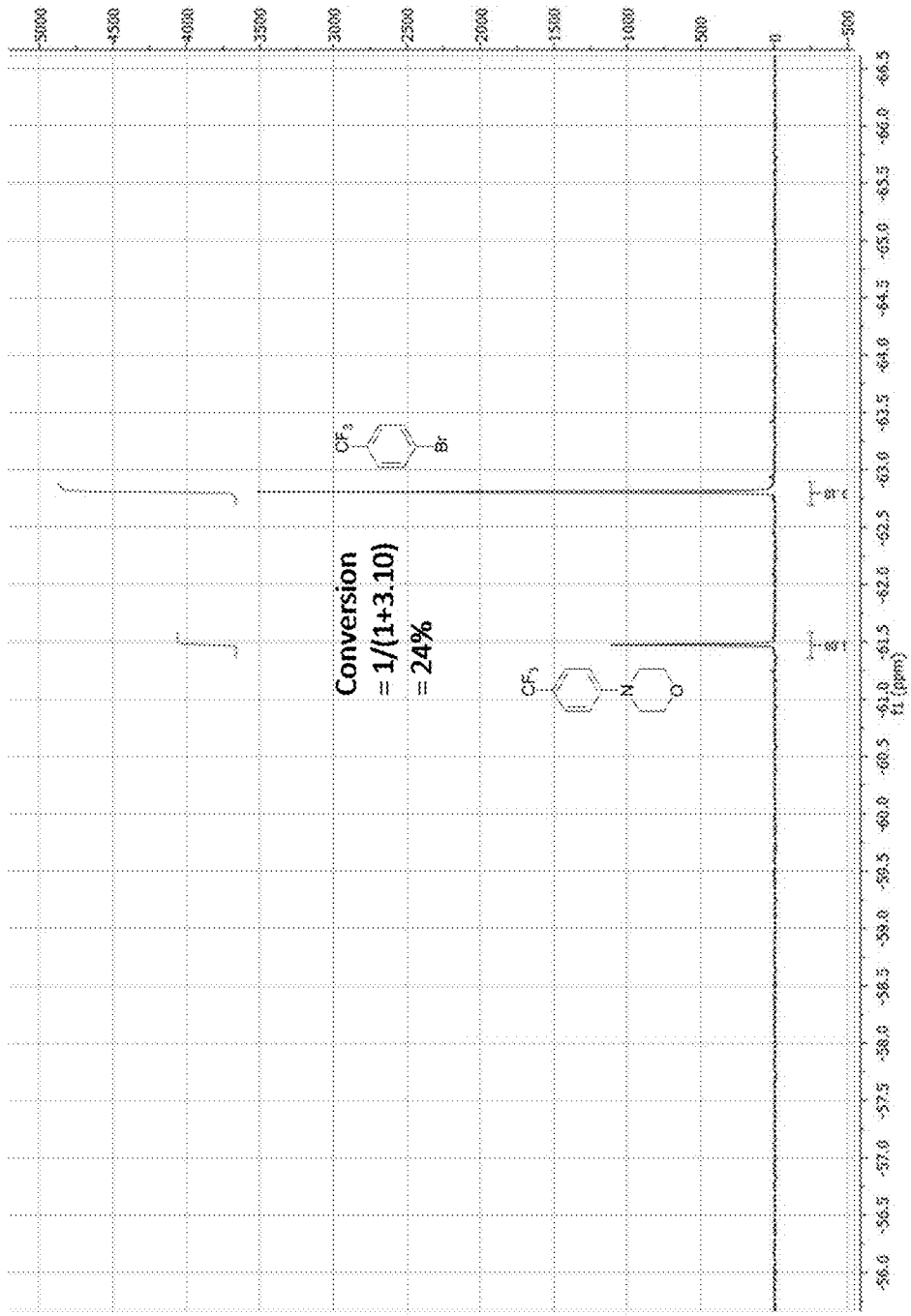
FIG. 5 depicts the conversion of the C—N coupled product determined from $^{19}F$ NMR in accordance with embodiments of the disclosure.

Model Substrates 4-bromobenzotrifluoride and morpholine were used as model substrates and employed General Procedure B to perform control experiments and reaction optimizations detailed below (Table 3, Table 4, Table 5, Table 6, Table 7, and Table 8). The conversion of the C—N coupled product (4-(4-(trifluoromethyl)phenyl)morpholine) was monitored as a function of time (e.g., 1 hour, 2 hours, and 3 hours) using $^{19}$F NMR (FIG. 5). Without being bound by theory, it was assumed that during the course of the reaction, the number of CF$_3$ groups in the reaction mixture is conserved, allowing the conversion of the C—N coupled product to be calculated (FIG. 5). This method was sufficiently accurate that $^{19}$F NMR conversion closely matches isolated yield. For example, C—N coupled product was isolated at 91% yield with $^{19}$F NMR conversion of 95%. To obtain $^{19}$F NMR conversion as a function of time, a ~10 μL aliquot was withdrawn from the reaction mixture under oxygen-free conditions and the sample was diluted with ~600 μl of deuterated chloroform before subjecting the sample to $^{19}$F NMR spectroscopy.

TABLE 3

Control experiment and effect of light source.

| hν | $^{19}$F-NMR Conversion | | |
|---|---|---|---|
| | 1 hour | 2 hour | 3 hour |
| No light | — | — | 0% |
| No light (80° C.) | — | — | 0% |
| 405 nm | 52% | 81% | 93% |
| 365 nm | 72% | 94% | 95% |
| | | | (91%)* |
| 365 nm (no nickel) | — | — | 0% |
| 365 nm (no base) | — | — | 55% |

*Isolated yield

TABLE 4

Effect of solvent.

| Solvent | $^{19}$F-NMR Conversion | | |
|---|---|---|---|
| | 1 hr | 2 hr | 3 hr |
| DMAc (365 nm) | 72% | 94% | 95% |
| | | | (91%)* |
| DMSO (365 nm) | — | — | 93% |
| MeOH (365 nm) | — | — | 60% |
| DMF (365 nm) | — | — | 93% |
| MeCN (365 nm) | — | — | 46% |

*Isolated yield

TABLE 5

Effect of types and loadings of nickel salts.

| Nickel salts | 19 F-NMR Conversion | | |
|---|---|---|---|
| | 1 hour | 2 hour | 3 hour |
| NiBr$_2$•glyme 5% | 81% | 96% | 95% |
| NiCl$_2$•6H$_2$O 5% | 76% | 96% | 95% |
| NiCl$_2$•glyme 5% | 68% | 95% | 95% |
| NiBr$_2$•3H$_2$O 5% | 72% | 94% | 95% (91%)* |
| NiBr$_2$•3H$_2$O 1% | 82% | 95% | 95% |
| NiBr$_2$•3H$_2$O 2% | 85% | 96% | 95% |
| NiBr$_2$•3H$_2$O 8% | 74% | 95% | 95% |
| NiBr$_2$•3H$_2$O 10% | 74% | 95% | 95% |

*Isolated yield

TABLE 6

Effect of added base.

| Base | 19 F-NMR Conversion | | |
|---|---|---|---|
| | 1 hour | 2 hour | 3 hour |
| quinuclidine 1.5 eq | 79% | 94% | 94% |
| DABCO 1.5 eq | 14% | 26% | 35% |
| DIPEA 1.5 eq | 21% | 48% | 68% |
| morpholine 1.5 eq | 20% | 47% | 64% |
| N-Me morpholine 1.5 eq | 31% | 46% | 52% |
| DMAP 1.5 eq | 0% | 1% | 2% |
| TEA 1.5 eq | 43% | 70% | 78% |
| DBU 1.5 eq | 0% | 0% | 2% |
| PMDETA 1.5 eq | 0% | 0% | 0% |
| Proton sponge 1.5 eq | 2% | 4% | 7% |

*Isolated yield

TABLE 7

Effect of nickel salts and added base.

| Base | Nickel | 19 F-NMR Conversion | | |
|---|---|---|---|---|
| | | 1 hour | 2 hour | 3 hour |
| morpholine 1.5 eq | NiBr$_2$•3H$_2$O 5% | 65% | 85% | 93% |
| morpholine 1.5 eq | NiBr$_2$•3H$_2$O 2% | 57% | 80% | 88% |
| morpholine 1.5 eq | NiBr$_2$•3H$_2$O 1% | 34% | 63% | 74% |
| morpholine 1.5 eq | NiCl$_2$•6H$_2$O 5% | 34% | 65% | 79% |
| morpholine 1.5 eq | NiCl$_2$•6H$_2$O 2% | 27% | 58% | 75% |
| morpholine 1.5 eq | NiCl$_2$•6H$_2$O 1% | 20% | 47% | 64% |
| DIPEA 1.5 eq | NiBr$_2$•3H$_2$O 5% | 45% | 79% | 85% |
| DIPEA 1.5 eq | NiBr$_2$•3H$_2$O 2% | 44% | 76% | 81% |
| DIPEA 1.5 eq | NiBr$_2$•3H$_2$O 1% | 23% | 50% | 68% |
| DIPEA 1.5 eq | NiCl$_2$•6H$_2$O 5% | 29% | 69% | 84% |
| DIPEA 1.5 eq | NiCl$_2$•6H$_2$O 2% | 28% | 65% | 79% |
| DIPEA 1.5 eq | NiCl$_2$•6H$_2$O 1% | 21% | 48% | 68% |
| TEA 1.5 eq | NiBr$_2$•3H$_2$O 5% | 51% | 77% | 86% |
| TEA 1.5 eq | NiBr$_2$•3H$_2$O 2% | 50% | 78% | 86% |
| TEA 1.5 eq | NiBr$_2$•3H$_2$O 1% | 36% | 65% | 77% |
| TEA 1.5 eq | NiCl$_2$•6H$_2$O 5% | 36% | 68% | 82% |
| TEA 1.5 eq | NiCl$_2$•6H$_2$O 2% | 31% | 64% | 81% |
| TEA 1.5 eq | NiCl$_2$•6H$_2$O 1% | 43% | 70% | 78% |

*Isolated yield

TABLE 8

Effect of base loading.

| Base | 19 F-NMR Conversion | | |
|---|---|---|---|
| | 1 hour | 2 hour | 3 hour |
| morpholine 0.0 eq | — | — | 55% |
| morpholine 1.0 eq | 52% | 75% | 84% |
| morpholine 1.5 eq | 65% | 85% | 93% |
| morpholine 1.8 eq | 63% | 86% | 94% |
| morpholine 2.0 eq | 66% | 90% | 94% |
| DIPEA 1.5 eq | 45% | 79% | 85% |
| DIPEA 1.8 eq | 27% | 66% | 83% |
| DIPEA 2.0 eq | 23% | 60% | 81% |
| TEA 1.5 eq | 51% | 77% | 86% |
| TEA 1.8 eq | 50% | 78% | 87% |

*Isolated yield

During reaction optimization, it was determined that no reaction occurred in the absence of nickel salts or without irradiation at either room temperature or 80° C. (Table 3). 405 nm light gave slower conversion than 365 nm light (52% vs. 72% at 1 hour) but achieved similar conversion at 3 hours. With no added quinuclidine, 55% conversion was obtained. DMF and DMSO gave similarly high conversion (>90%) to DMAc, while MeOH and MeCN gave considerably lower conversion (Table 4). Various nickel salts at different loadings have similar performance (Table 5). The effect of types of added organic bases were also investigated (Table 6 and Table 7). Quinuclidine gave the best performance while bases such as DMAP, DBU, and PMDETA almost completely shut off reactivity. Table 8 shows that excess morpholine substrate can also function as a base. For example, when morpholine substrate was introduced at 3.5 equivalents, 94% of conversion was obtained with no added base.

UV-Visible Spectroscopy

Figure 6:
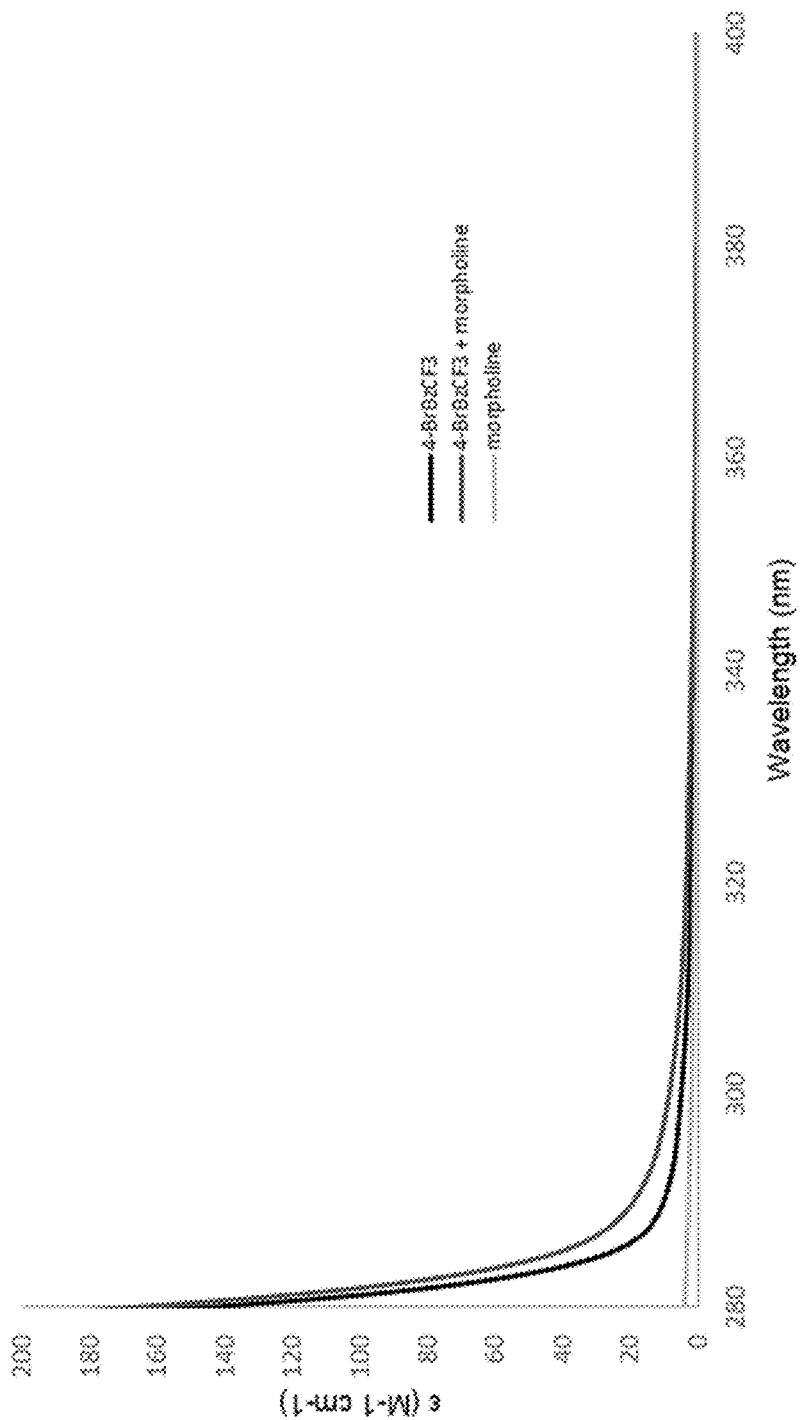
FIG. 6 depicts the molar absorptivity vs. wavelength for 4-bromobenzotrifluoride and morpholine individually and combined in DMAc, 0.4 M in 4-bromobenzotrifluoride and 1.4 M in morpholine in accordance with embodiments of the disclosure.

UV-visible spectroscopy was performed for each reaction component and combination of reaction components using a Cary 5000 spectrophotometer (Agilent Technologies). Morpholine and 4-bromobenzotrifluoride (4-BrBzCF$_3$) are both colorless liquids without significant molar absorptivity at wavelengths greater than 300 nm (FIG. 6) at the concentrations present in the C—N coupling reaction mixture.

Figure 7:
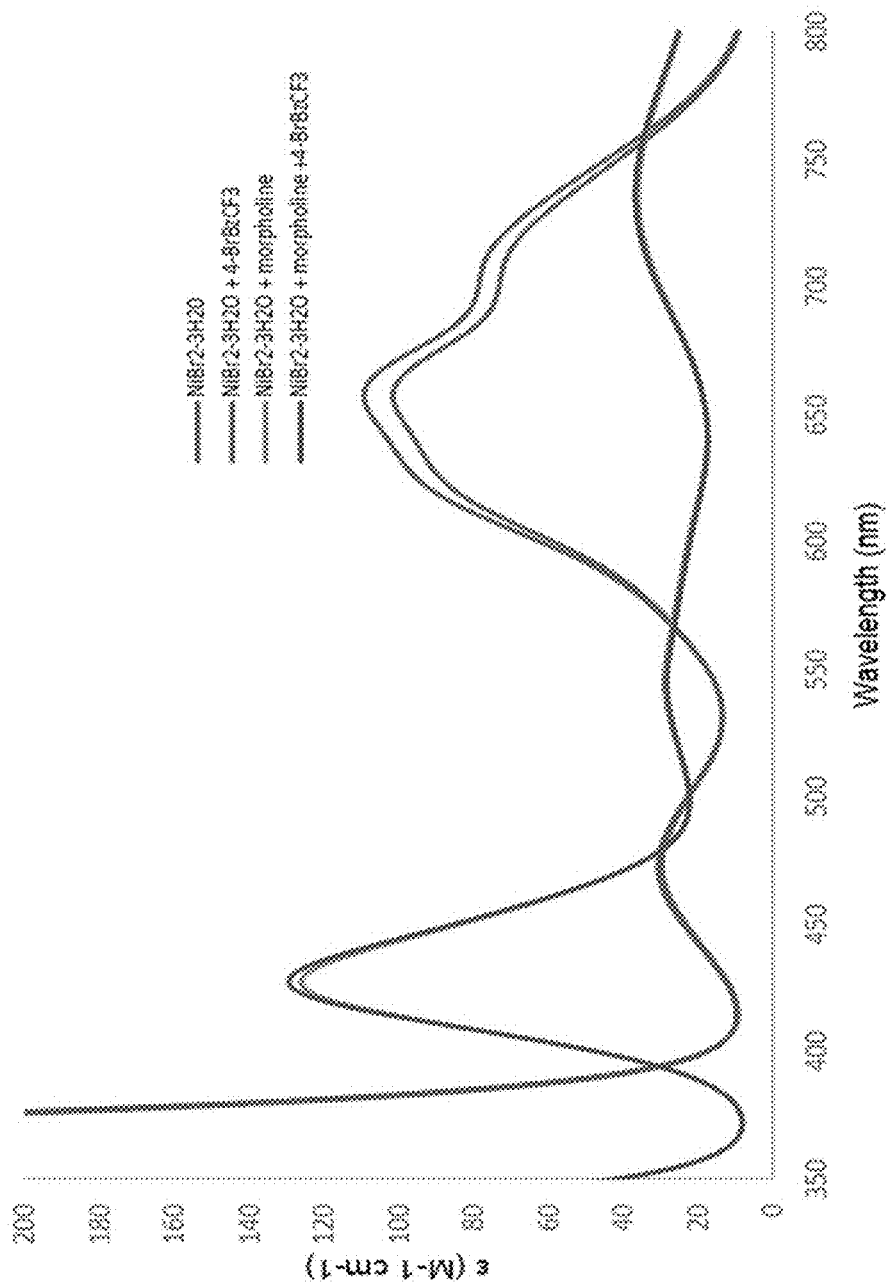
FIG. 7 depicts the molar absorptivity vs. wavelength for $NiBr_2 \cdot 3H_2O$ and its combinations with 4-bromobenzotrifluoride and morpholine in DMAc in accordance with embodiments of the disclosure.
Figure 8:
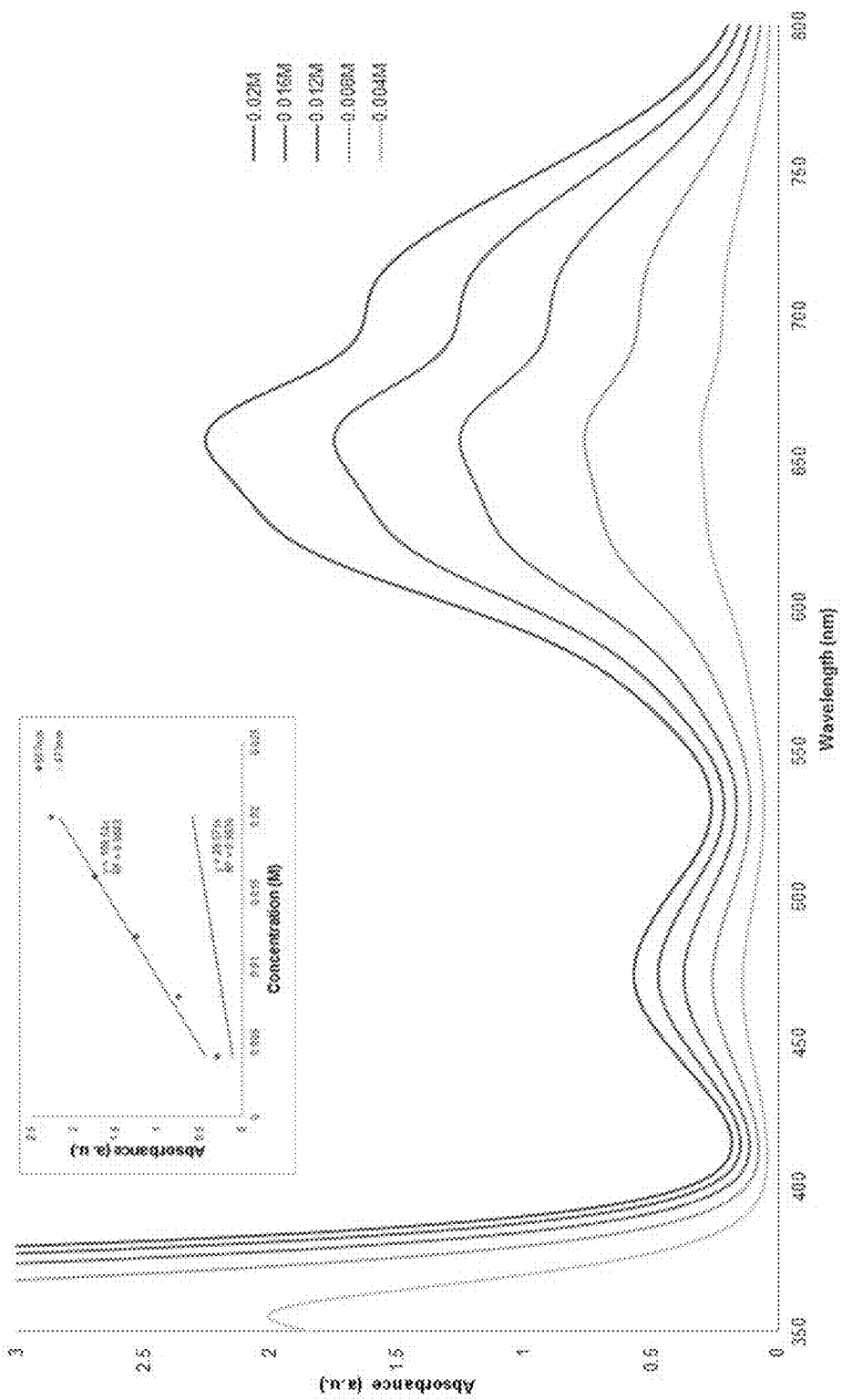
FIG. 8 depicts the absorption spectra of $NiBr_2 \cdot 3H_2O$ at concentrations ranging from 0.02-0.004 M in DMAC. Inset: a photo of the solution and linear regressions at 657 nm and 473 nm in accordance with embodiments of the disclosure.
Figure 9:
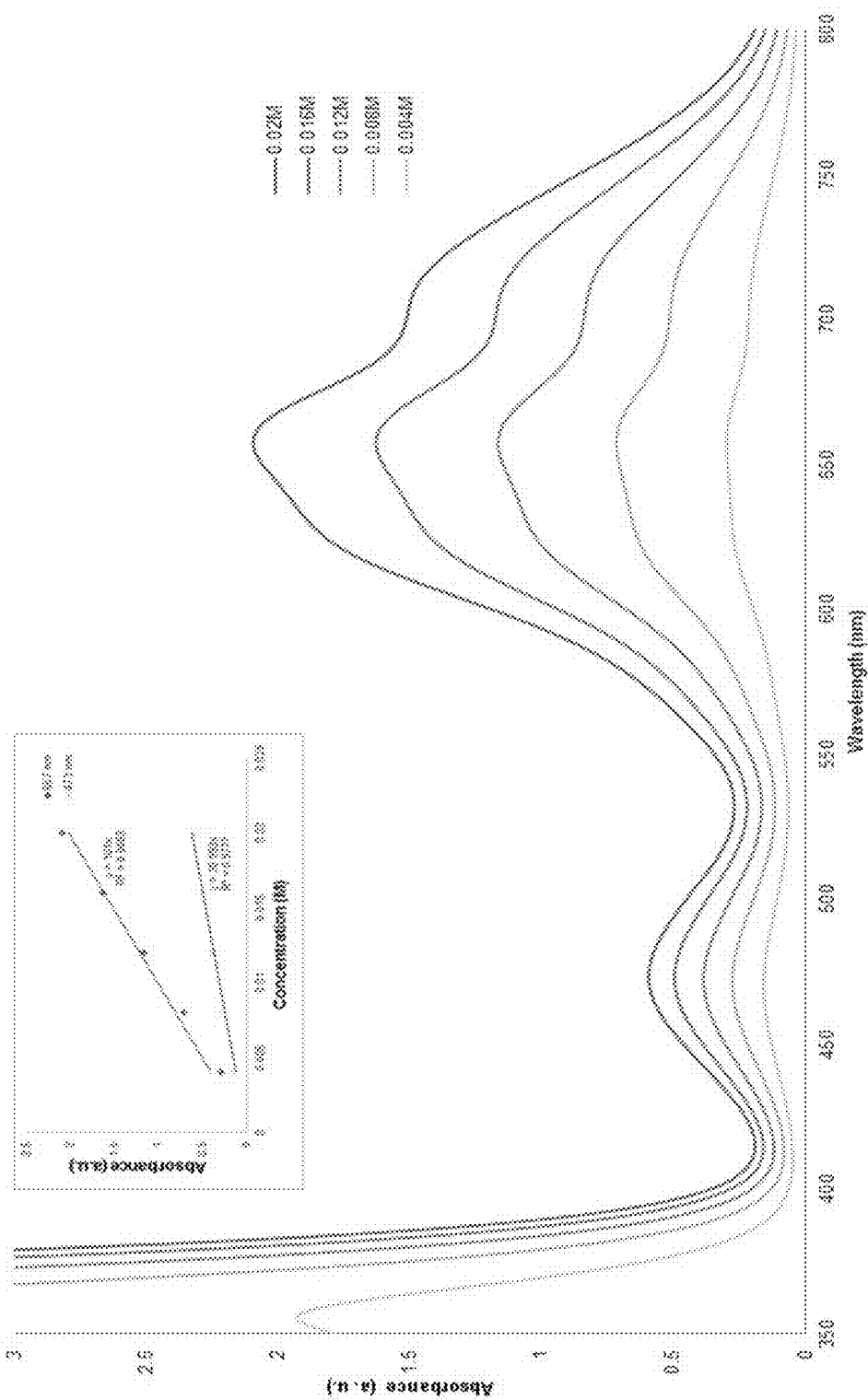
FIG. 9 depicts the absorption spectra of $NiBr_2 \cdot 3H_2O+4-BrBzCF_3$ at concentrations ranging from 0.02-0.004 M ($NiBr_2 \cdot 3H_2O$) and 0.4-0.08 M ($4-BrBzCF_3$) in DMAC. Inset: linear regressions at 657 nm and 473 nm in accordance with embodiments of the disclosure.
Figure 10:
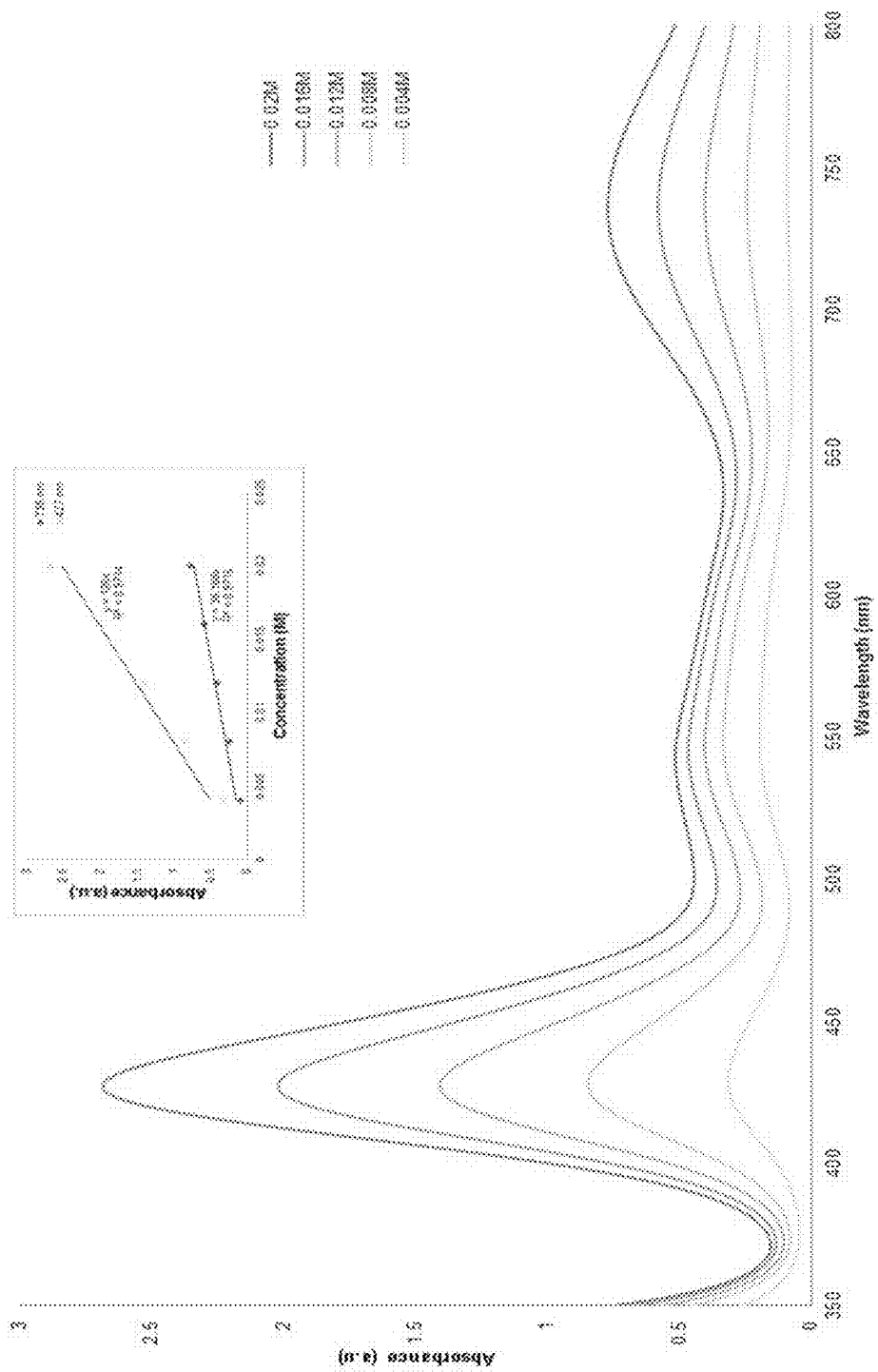
FIG. 10 depicts the absorption spectra of $NiBr_2 \cdot 3H_2O$+ morpholine at concentrations ranging from 0.02-0.004 M ($NiBr_2 \cdot 3H_2O$) and 1.4-0.28 M (morpholine) in DMAc. Inset: a photo of the mixture and linear regressions at 736 nm and 427 nm in accordance with embodiments of the disclosure.
Figure 11:
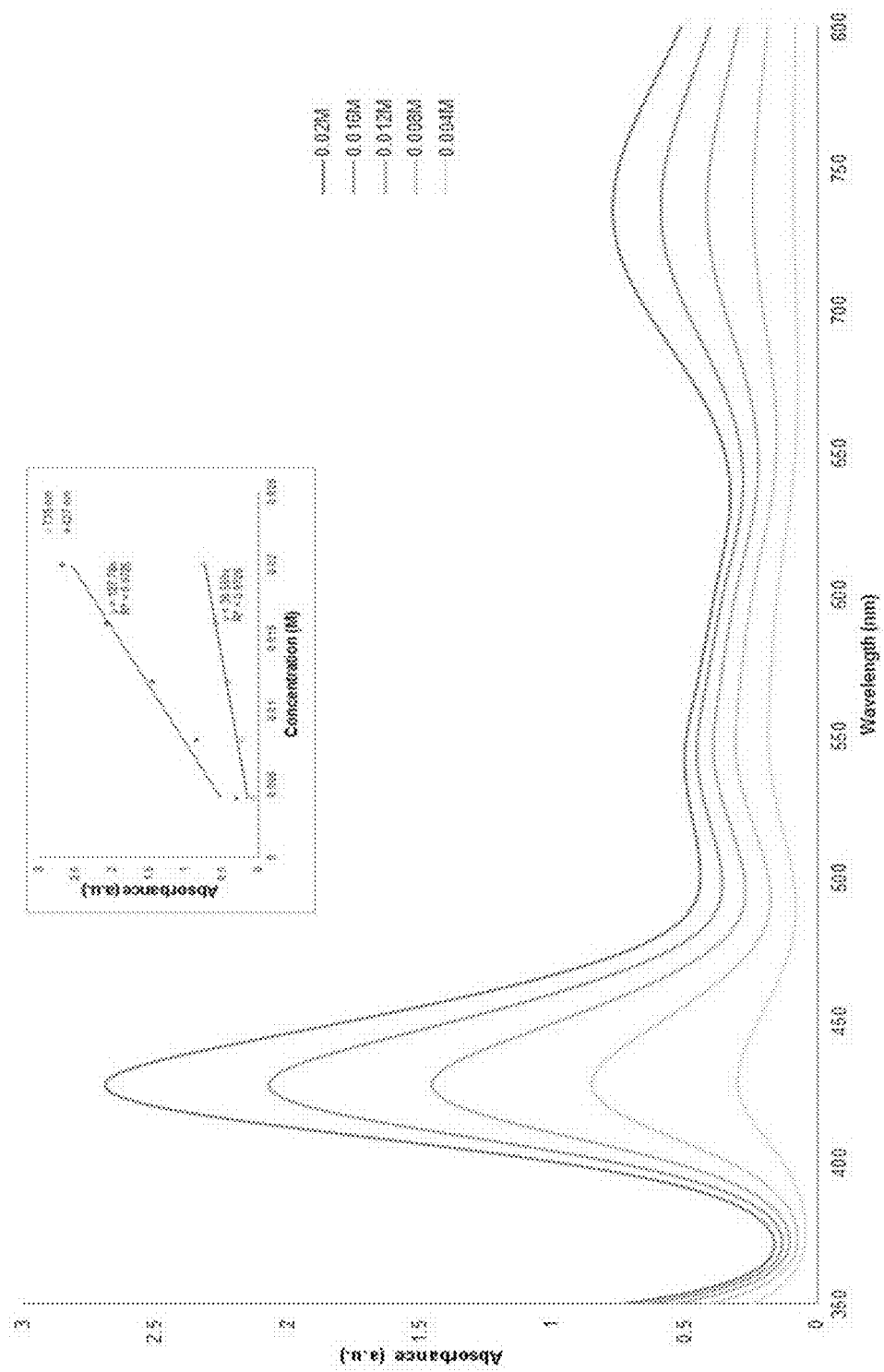
FIG. 11 depicts the absorption spectra of $NiBr_2 \cdot 3H_2O$+ morpholine+4-$BrBzCF_3$ at concentrations ranging from 0.02-0.004 M ($NiBr_2 \cdot 3H_2O$), 1.4-0.28 M (morpholine), and 0.4-0.08 M (4-$BrBzCF_3$) in DMAC. Inset: linear regressions at 736 nm and 427 nm in accordance with embodiments of the disclosure.

UV-visible spectroscopy was also performed for NiBr$_2$.3H$_2$O alone and in combination with 4-BrBzCF$_3$ and morpholine. NiBr$_2$.3H$_2$O has a distinctive absorption profile which was not altered with addition of 4-BrBzCF$_3$. However, upon addition of morpholine, the $\lambda_{max}$ was blue-shifted from 657 nm to 427 nm (FIG. 7).

Molar absorptivity for each major peak and secondary peak of each combination were calculated according to Beer's Law (Table 10) with 5 data points used for each reported value (FIG. 8, FIG. 9, FIG. 10, and FIG. 11). The $R^2$ coefficient of determination is also reported for each peak.

TABLE 10

Molar absorptivity for the most prominent peaks of each reagent combination. Data was extracted from spectra collected for 5 concentrations ranging from 0.02-0.008M in NiBr$_2$•3H$_2$O.

| Solution | $\lambda_{max}$ (nm) | $\lambda_2$ (nm) | $\varepsilon_{max}$ (s$^{-1}$M$^{-1}$) | $\varepsilon_2$ (s$^{-1}$M$^{-1}$) | $R_{max}^2$ | $R_2^2$ |
|---|---|---|---|---|---|---|
| NiBr$_2$•3H$_2$O | 657 | 473 | 109 | 30 | .984 | .984 |
| NiBr$_2$•3H$_2$O + morpholine | 427 | 736 | 126 | 36 | .971 | .971 |

TABLE 10-continued

Molar absorptivity for the most prominent peaks of each reagent combination. Data was extracted from spectra collected for 5 concentrations ranging from 0.02-0.008M in NiBr$_2$•3H$_2$O.

| Solution | $\lambda_{max}$ (nm) | $\lambda_2$ (nm) | $\varepsilon_{max}$ (s$^{-1}$M$^{-1}$) | $\varepsilon_2$ (s$^{-1}$M$^{-1}$) | $R_{max}^2$ | $R_2^2$ |
|---|---|---|---|---|---|---|
| NiBr$_2$•3H$_2$O + 4-BrBzCF$_3$ | 657 | 473 | 101 | 31 | .986 | .977 |
| NiBr$_2$•3H$_2$O + morpholine + 4-BrBzCF$_3$ | 427 | 736 | 128 | 37 | .973 | .973 |

Computational Details

All calculations were performed using computational chemistry software package GAUSSIAN 09 ver. D01.

Geometries of all molecular structures were optimized at the uM06/6-31+G(d,p)/CPCM-DMAc level of theory followed by frequency calculations to obtain zero point energy (ZPE) corrections, thermal corrections, and entropic TS terms using ideal gas approximations. The obtained Gibbs free energy, G$^0$*(298K, 1 atm), by default has a standard reference state of 298.15K and 1 atm. However, a standard reference state of 298.15K and 1 mole/liter [G$^0$(298K, 1 M)] is more relevant to our examined systems as the C—N cross-coupling reactions are carried out in the liquid phase in DMAc.

To obtain the Gibbs free energy with relevant standard state reference, G$^0$(298K, 1 M)=G$^0$*(298K, 1 atm)+RT ln(0.08206 T), where R is the gas constant and T is the temperature. $\Delta$G$^0$(298K, 1 M)=$\Delta$G$^0$*(298K, 1 atm) when there is no mole change from the reactant to the product. However, for every net mole change $\Delta$G$^0$(298K, 1 M)=$\Delta$G$^0$*(298K, 1 atm)−1.89 kcal/mol.

At the converged geometries, single point calculations at uM06/6-311+G(d,p)/CPCM-DMAc were performed; the various corrections and entropic TS terms from uM06/6-31+G(d,p) calculations were then applied to the energy obtained with uM06/6-311+G(d,p).

Characterizations

Synthesis of 4-(4-(trifluoromethyl)phenyl)morpholine (1a)

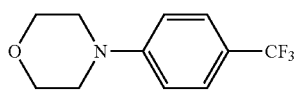

General Procedure A was followed using 4-bromobenzotrifluoride as the aryl halide, and morpholine as the amine. The reaction was run at room temperature for 3 hours. Purification was done by flash chromatography on silica gel, eluting with a gradient of 0-15% EtOAc/hexanes to give the product as a white solid (80.2 mg, 87%). NMR data matched previously reported spectra.[35,36] $^1$H NMR (400 MHz, Chloroform-d) δ 7.50 (d, J=8.4 Hz, 2H), 6.92 (d, J=8.8 Hz, 2H), 3.86 (t, J=4.8 Hz, 4H), 3.24 (t, J=5.2 Hz, 4H). $^{13}$C NMR (101 MHz, Chloroform-d) δ 153.5, 126.6 (q, J$_{C-F}$=3.8 Hz), 124.8 (q, J$_{C-F}$=271.7 Hz), 121.1 (q, J$_{C-F}$=32.9 Hz), 114.4, 66.8, 48.3. $^{19}$F NMR (376 MHz, Chloroform-d) δ −61.4 (s, 3F). HRMS (DART-TOF): calculated for C$_{11}$H$_{13}$F$_3$NO ([M+H]$^+$) 232.0944, found 232.0943.

Synthesis of 1-(4-(trifluoromethyl)phenyl)piperidine (2)

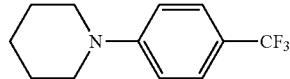 [SMILES: FC(F)(F)c1ccc(N2CCCCC2)cc1]

General Procedure A was followed using 4-bromobenzotrifluoride as the aryl halide, and piperidine as the amine. The reaction was run at room temperature for 3 hours. Purification was done by flash chromatography on silica gel, eluting with a gradient of 0-15% EtOAc/hexanes to give the product as a pale yellow oil (74.5 mg, 81%). NMR data matched previously reported spectra.[37] $^1$H NMR (400 MHz, Chloroform-d) δ 7.46 (d, J=8.7 Hz, 2H), 6.92 (d, J=8.7 Hz, 2H), 3.27 (t, J=5.2 Hz, 4H), 1.77-1.58 (m, 6H). $^{13}$C NMR (101 MHz, Chloroform-d) δ 154.0, 126.5 (q, J$_{C-F}$=3.7 Hz), 124.9 (q, J$_{C-F}$=271.6 Hz), 119.7 (q, J$_{C-F}$=32.7 Hz), 114.7, 49.4, 25.6, 24.4. $^{19}$F NMR (376 MHz, Chloroform-d) δ −61.2 (s, 3F). HRMS (DART-TOF): calculated for C$_{12}$H$_{15}$F$_3$N ([M+H]$^+$) 231.1151, found 230.1162.

Synthesis of 4-methyl-1-(4-(trifluoromethyl)phenyl)piperidine (3)

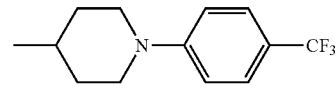

General Procedure A was followed using 4-bromobenzotrifluoride as the aryl halide, and 4-methylpiperidine as the amine. The reaction was run at room temperature for 3 hours. Purification was done by flash chromatography on silica gel, eluting with a gradient of 0-15% EtOAc/hexanes to give the product as a white solid (84.4 mg, 87%). $^1$H NMR (400 MHz, Chloroform-d) δ 7.46 (d, J=8.4 Hz, 2H), 6.92 (d, J=8.6 Hz, 2H), 3.83-3.72 (m, 2H), 2.80 (td, J=12.5, 2.7 Hz, 2H), 1.80-1.69 (m, 2H), 1.67-1.49 (m, 1H), 1.39-1.23 (m, 2H), 0.99 (d, J=6.5 Hz, 3H). $^{13}$C NMR (101 MHz, Chloroform-d) δ 153.7, 126.5 (q, J$_{C-F}$=3.7 Hz), 125.0 (q, J$_{C-F}$=271.4 Hz), 119.6 (q, J$_{C-F}$=32.7 Hz), 114.7, 48.8, 33.8, 30.9, 22.0. $^{19}$F NMR (376 MHz, Chloroform-d) δ −61.2 (s, 3F). HRMS (DART-TOF): calculated for C$_{13}$H$_{17}$F$_3$N ([M]) 244.1308, found 244.1307.

1-(4-(trifluoromethyl)phenyl)piperidine-4-carbonitrile (4)

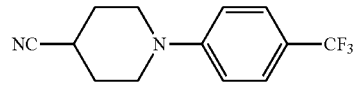 [SMILES: N#CC1CCN(c2ccc(C(F)(F)F)cc2)CC1]

General Procedure A was followed using 4-bromobenzotrifluoride as the aryl halide, and piperidine-4-carbonitrile as the amine. The reaction was run at room temperature for 3 hours. Purification was done by flash chromatography on silica gel, eluting with a gradient of 0-15% EtOAc/hexanes to give the product as a white solid (89.7 mg, 88%). NMR data matched previously reported spectra.[37] $^1$H NMR (400

MHz, Chloroform-d) δ 7.49 (d, J=8.6 Hz, 2H), 6.93 (d, J=8.5 Hz, 2H), 3.57-3.46 (m, 2H), 3.28-3.17 (m, 2H), 2.85 (tt, J=8.0, 4.3 Hz, 1H), 2.12-1.91 (m, 4H). $^{13}$C NMR (101 MHz, Chloroform-d) δ 153.1, 126.6 (q, $J_{C-F}$=3.7 Hz), 124.7 (q, $J_{C-F}$=272.0 Hz), 121.3 (q, $J_{C-F}$=33.1 Hz), 121.2, 115.4, 46.9, 28.3, 26.3. $^{19}$F NMR (376 MHz, Chloroform-d) δ −61.5 (s, 3F). HRMS (DART-TOF): calculated for $C_{13}H_{14}F_3N_2$ ([M+H]$^+$) 255.1104, found 255.1093.

Synthesis of 1-(4-(trifluoromethyl)phenyl)piperidin-4-ol (5)

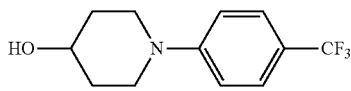 [SMILES: OC1CCN(c2ccc(C(F)(F)F)cc2)CC1]

General Procedure A was followed using 4-bromobenzotrifluoride as the aryl halide, and 4-hydroxypiperidine as the amine. The reaction was run at room temperature for 3 hours. Purification was done by flash chromatography on silica gel, eluting with a gradient of 0-40% EtOAc/hexanes to give the product as a white solid (82.4 mg, 84%). NMR data matched previously reported spectra.[37] $^1$H NMR (400 MHz, Chloroform-d) δ 7.46 (d, J=8.7 Hz, 2H), 6.92 (d, J=8.8 Hz, 2H), 3.89 (tt, J=8.7, 4.0 Hz, 1H), 3.74-3.56 (m, 2H), 3.03 (ddd, J=13.0, 9.7, 3.2 Hz, 2H), 2.06-1.92 (m, 2H), 1.79 (s, 1H), 1.74-1.53 (m, 2H). $^{13}$C NMR (101 MHz, Chloroform-d) δ 153.1, 126.5 (q, $J_{C-F}$=3.8 Hz), 124.9 (q, $J_{C-F}$=271.5 Hz), 120.1 (q, $J_{C-F}$=32.7 Hz), 114.9, 67.7, 46.0, 33.8. $^{19}$F NMR (376 MHz, Chloroform-d) δ −61.3 (s, 3F). HRMS (DART-TOF): calculated for $C_{12}H_{15}F_3NO$ ([M+H]$^+$) 246.1100, found 246.1099.

Synthesis of methyl 1-(4-(trifluoromethyl)phenyl)piperidine-4-carboxylate (6)

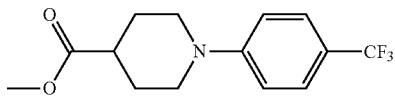

General Procedure A was followed using 4-bromobenzotrifluoride as the aryl halide, and methyl 4-piperidinecarboxylate as the amine. The reaction was run at room temperature for 3 hours. Purification was done by flash chromatography on silica gel, eluting with a gradient of 0-15% EtOAc/hexanes to give the product as a white solid (78.8 mg, 69%). $^1$H NMR (400 MHz, Chloroform-d) δ 7.46 (d, J=8.7 Hz, 2H), 6.92 (d, J=8.6 Hz, 2H), 3.80-3.68 (m, 5H), 2.90 (ddd, J=12.7, 11.3, 2.9 Hz, 2H), 2.51 (tt, J=11.0, 4.0 Hz, 1H), 2.08-1.97 (m, 2H), 1.92-1.77 (m, 2H). $^{13}$C NMR (101 MHz, Chloroform-d) δ 175.1, 153.4, 126.5 (q, $J_{C-F}$=3.8 Hz), 124.9 (q, $J_{C-F}$=271.7 Hz), 120.3 (q, $J_{C-F}$=32.8 Hz), 115.0, 51.9, 48.0, 40.9, 27.8. $^{19}$F NMR (376 MHz, Chloroform-d) δ −61.3 (s, 3F). HRMS (DART-TOF): calculated for $C_{14}H_{17}F_3NO_2$ ([M+H]$^+$) 288.1206, found 288.1210.

Synthesis of 1-(4-(trifluoromethyl)phenyl)pyrrolidine (7)

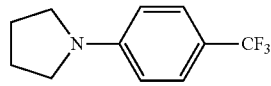 [SMILES: FC(F)(F)c1ccc(N2CCCC2)cc1]

General Procedure A was followed using 4-bromobenzotrifluoride as the aryl halide, and pyrrolidine as the amine. The reaction was run at room temperature for 3 hours. Purification was done by flash chromatography on silica gel, eluting with a gradient of 0-15% EtOAc/hexanes to give the product as a white solid (66.0 mg, 77%). NMR data matched previously reported spectra.[35,36] $^1$H NMR (400 MHz, Chloroform-d) δ 7.44 (d, J=8.6 Hz, 2H), 6.55 (d, J=8.6 Hz, 2H), 3.36-3.27 (m, 4H), 2.10-1.97 (m, 4H). $^{13}$C NMR (101 MHz, Chloroform-d) δ 149.9, 126.5 (q, $J_{C-F}$=3.7 Hz), 125.5 (q, $J_{C-F}$=270.5 Hz), 116.8 (q, $J_{C-F}$=32.5 Hz), 111.0, 47.7, 25.6. $^{19}$F NMR (376 MHz, Chloroform-d) δ −60.6 (s, 3F). HRMS (DART-TOF): calculated for $C_{11}H_{13}F_3N$ ([M+H]$^+$) 216.0995, found 216.1001.

Synthesis of 1-(4-(trifluoromethyl)phenyl)piperazine (8)

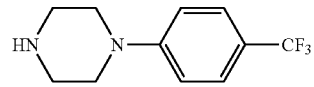

General Procedure A was followed using 4-bromobenzotrifluoride as the aryl halide, and piperazine as the amine. DMSO was used as the solvent instead of DMAc. The reaction was run at room temperature for 15 hours. Purification was done by flash chromatography on silica gel, eluting with a gradient of 0-20% MeOH/DCM to give the product as a pale yellow solid (56.1 mg, 61%). NMR data matched previously reported spectra.[38] $^1$H NMR (400 MHz, Chloroform-d) δ 7.47 (d, J=8.5 Hz, 2H), 6.91 (d, J=8.6 Hz, 2H), 3.23 (t, J=4.8 Hz, 4H), 3.02 (t, J=5.0 Hz, 4H), 1.81 (s, 1H). $^{13}$C NMR (101 MHz, Chloroform-d) δ 153.9, 126.5 (q, $J_{C-F}$=3.8 Hz), 124.9 (q, $J_{C-F}$=271.9 Hz), 120.6 (q, $J_{C-F}$=32.6 Hz), 114.6, 49.2, 46.0. $^{19}$F NMR (376 MHz, Chloroform-d) δ −61.4 (s, 3F). HRMS (DART-TOF): calculated for $C_{11}H_{14}F_3N_2$ ([M+H]$^+$) 231.1104, found 231.1101.

Synthesis of tert-butyl 4-(4-(trifluoromethyl)phenyl)piperazine-1-carboxylate (9)

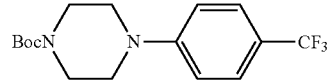

General Procedure B was followed using 4-bromobenzotrifluoride as the aryl halide, and tert-butyl piperazine-1-carboxylate as the amine. The reaction was run at room temperature for 3 hours. Purification was done by flash chromatography on silica gel, eluting with a gradient of 0-15% EtOAc/hexanes to give the product as a white solid (112.4 mg, 85%). NMR data matched previously reported spectra.[35,37] $^1$H NMR (400 MHz, Chloroform-d) δ 7.49 (d, J=8.0 Hz, 2H), 6.92 (d, J=8.4 Hz, 2H), 3.58 (t, J=4.8 Hz, 4H), 3.23 (t, J=5.6 Hz, 4H), 1.49 (s, 9H). $^{13}$C NMR (101 MHz, Chloroform-d) δ 154.8, 153.3, 126.6 (q, $J_{C-F}$=3.7 Hz), 124.8 (q, $J_{C-F}$=271.7 Hz), 121.1 (q, $J_{C-F}$=32.8 Hz), 115.1, 80.2, 48.2, 28.5. $^{19}$F NMR (376 MHz, Chloroform-d) δ −61.4 (s, 3F). HRMS (DART-TOF): calculated for $C_{16}H_{22}F_3N_2O_2$ ([M+H]$^+$) 331.1628, found 331.1630.

Synthesis of N-cyclohexyl-4-(trifluoromethyl)aniline (10)

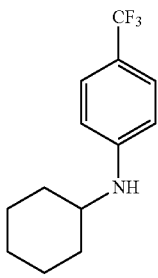 [SMILES: FC(F)(F)c1ccc(NC2CCCCC2)cc1]

General Procedure A was followed using 4-bromobenzotrifluoride as the aryl halide, and cyclohexylamine as the amine. The reaction was run at room temperature for 15 hours. Purification was done by flash chromatography on silica gel, eluting with a gradient of 0-15% EtOAc/hexanes to give the product as a pale yellow solid (68.1 mg, 70%). NMR data matched previously reported spectra.[35,37] $^1$H NMR (400 MHz, Chloroform-d) δ 7.38 (d, J=8.5 Hz, 2H), 6.57 (d, J=8.5 Hz, 2H), 3.88 (d, J=7.8 Hz, 1H), 3.38-3.20 (m, 1H), 2.13-1.96 (m, 2H), 1.86-1.72 (m, 2H), 1.73-1.59 (m, 1H), 1.47-1.32 (m, 2H), 1.32-1.07 (m, 3H). $^{13}$C NMR (101 MHz, Chloroform-d) δ 149.9, 126.8 (q, $J_{C-F}$=3.8 Hz), 125.2 (q, $J_{C-F}$=271.1 Hz), 118.2 (q, $J_{C-F}$=32.7 Hz), 112.10, 51.5, 33.3, 25.9, 25.0. $^{19}$F NMR (376 MHz, Chloroform-d) δ −60.9 (s, 3F). HRMS (DART-TOF): calculated for $C_{13}H_{17}F_3N$ ([M+H]$^+$) 244.1308, found 244.1293.

Synthesis of N-propyl-4-(trifluoromethyl)aniline (11)

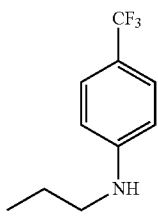

General Procedure A was followed using 4-bromobenzotrifluoride as the aryl halide, and propylamine as the amine. The reaction was run at room temperature for 15 hours. Purification was done by flash chromatography on silica gel, eluting with a gradient of 0-15% EtOAc/hexanes to give the product as a pale yellow oil (33.1 mg, 41%). NMR data matched previously reported spectra.[36] $^1$H NMR (400 MHz, Chloroform-d) δ 7.39 (d, J=8.4 Hz, 2H), 6.59 (d, J=8.5 Hz, 2H), 3.97 (s, 1H), 3.11 (q, J=5.2 Hz, 2H), 1.66 (h, J=7.2 Hz, 2H), 1.01 (t, J=7.4 Hz, 3H). $^{13}$C NMR (101 MHz, Chloroform-d) δ 151.0, 126.7 (q, $J_{C-F}$=3.7 Hz), 125.2 (q, $J_{C-F}$=271.2 Hz), 118.6 (q, $J_{C-F}$=32.7 Hz), 111.8, 45.4, 22.75, 11.7. $^{19}$F NMR (376 MHz, Chloroform-d) δ −60.9 (s, 3F). HRMS (DART-TOF): calculated for $C_{10}H_{13}F_3N$ ([M+H]$^+$) 204.0995, found 204.0989.

Synthesis of N-hexyl-4-(trifluoromethyl)aniline (12)

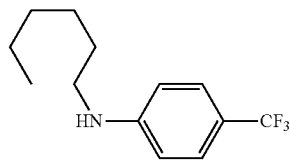 [SMILES: CCCCCCNc1ccc(C(F)(F)F)cc1]

General Procedure A was followed using 4-bromobenzotrifluoride as the aryl halide, and hexylamine as the amine. The reaction was run at room temperature for 15 hours. Purification was done by flash chromatography on silica gel, eluting with a gradient of 0-15% EtOAc/hexanes to give the product as a pale yellow oil (55.9 mg, 57%). NMR data matched previously reported spectra.[35] $^1$H NMR (400 MHz, Chloroform-d) δ 7.40 (d, J=8.5 Hz, 2H), 6.59 (d, J=8.5 Hz, 2H), 3.94 (s, 1H), 3.29-2.97 (m, 2H), 1.63 (p, J=7.1 Hz, 2H), 1.46-1.28 (m, 6H), 1.00-0.83 (m, 3H). $^{13}$C NMR (101 MHz, Chloroform-d) δ 151.0, 126.7 (q, $J_{C-F}$=3.9 Hz), 125.2 (q, $J_{C-F}$=271.2 Hz), 118.5 (q, $J_{C-F}$=32.7 Hz), 111.8, 43.7, 31.7, 29.4, 26.9, 22.8, 14.2. $^{19}$F NMR (376 MHz, Chloroform-d) δ −60.9 (s, 3F). HRMS (DART-TOF): calculated for $C_{13}H_{19}F_3N$ ([M+H]$^+$) 246.1464, found 246.1462.

Synthesis of N-phenethyl-4-(trifluoromethyl)aniline (13)

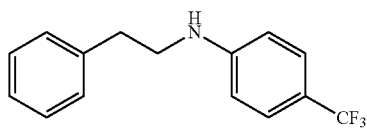 [SMILES: FC(F)(F)c1ccc(NCCc2ccccc2)cc1]

General Procedure B was followed using 4-bromobenzotrifluoride as the aryl halide, and phenethylamine as the amine. The reaction was run at room temperature for 15 hours. Purification was done by flash chromatography on silica gel, eluting with a gradient of 0-15% EtOAc/hexanes to give the product as a yellow oil (34.9 mg, 33%). NMR data matched previously reported spectra.[39] $^1$H NMR (400 MHz, Chloroform-d) δ 7.44 (d, J=8.5 Hz, 2H), 7.40-7.33 (m, 2H), 7.32-7.22 (m, 3H), 6.63 (d, J=8.5 Hz, 2H), 4.04 (s, 1H), 3.47 (q, J=6.6 Hz, 2H), 2.96 (t, J=6.9 Hz, 2H). $^{13}$C NMR (101 MHz, Chloroform-d) δ 150.5, 138.9, 128.89, 128.86, 126.78 (q, $J_{C-F}$=3.9 Hz), 126.77, 125.1 (q, $J_{C-F}$=271.3 Hz), 119.0 (q, $J_{C-F}$=32.8 Hz), 112.1, 44.6, 35.4. $^{19}$F NMR (376 MHz, Chloroform-d) δ −61.0 (s, 3F). HRMS (DART-TOF): calculated for $C_{15}H_{15}F_3N$ ([M+H]$^+$) 266.1151, found 266.1154.

Synthesis of N-phenyl-4-(trifluoromethyl)aniline (14)

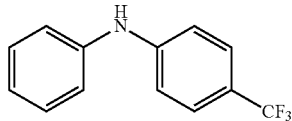

General Procedure B was followed using 4-bromobenzotrifluoride as the aryl halide, and aniline as the amine. The reaction was run at room temperature for 15 hours. Purification was done by flash chromatography on silica gel, eluting with a gradient of 0-10% EtOAc/hexanes to give the product as a pale yellow solid (63.8 mg, 67%). NMR data matched previously reported spectra.[35,36] $^1$H NMR (400 MHz, Chloroform-d) δ 7.49 (d, J=8.5 Hz, 2H), 7.36 (t, J=8.4 Hz, 2H), 7.16 (d, J=7.2 Hz, 2H), 7.12-7.02 (m, 3H), 5.91 (s, 1H). $^{13}$C NMR (101 MHz, Chloroform-d) δ 146.9, 141.3, 129.7, 126.8 (q, $J_{C-F}$=3.9 Hz), 124.8 (q, $J_{C-F}$=271.8 Hz), 123.1, 121.8 (q, $J_{C-F}$=32.8 Hz), 120.2, 115.5. $^{19}$F NMR (376 MHz, Chloroform-d) δ -61.4 (s, 3F). HRMS (DART-TOF): calculated for $C_{13}H_{11}F_3N$ ([M+H]$^+$) 238.0838, found 238.0826.

Synthesis of 4-fluoro-N-(4-(trifluoromethyl)phenyl)aniline (15)

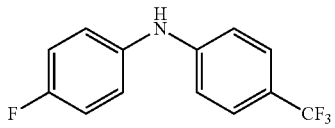 [SMILES: Fc1ccc(Nc2ccc(C(F)(F)F)cc2)cc1]

General Procedure B was followed using 4-bromobenzotrifluoride as the aryl halide, and 4-Fluoroaniline as the amine. The reaction was run at room temperature for 15 hours. Purification was done by flash chromatography on silica gel, eluting with a gradient of 0-10% EtOAc/hexanes to give the product as a yellow oil (46.9 mg, 46%). $^1$H NMR (400 MHz, Chloroform-d) δ 7.46 (d, J=8.5 Hz, 2H), 7.18-7.08 (m, 2H), 7.08-6.99 (m, 2H), 6.93 (d, J=8.4 Hz, 2H), 5.79 (s, 1H). $^{13}$C NMR (101 MHz, Chloroform-d) δ 159.3 (d, $J_{C-F}$=243.6 Hz), 147.7, 137.1 (d, $J_{C-F}$=2.7 Hz), 126.9 (q, $J_{C-F}$=3.9 Hz), 124.8 (q, $J_{C-F}$=271.8 Hz), 123.2 (d, $J_{C-F}$=8.1 Hz), 121.5 (q, $J_{C-F}$=32.8 Hz), 116.4 (d, $J_{C-F}$=22.7 Hz), 114.7. $^{19}$F NMR (376 MHz, Chloroform-d) δ -61.4 (s, 3F), -119.2 (m, 1F). HRMS (DART-TOF): calculated for $C_{13}H_{10}F_4N$ ([M+H]$^+$) 256.0744, found 256.0737.

Synthesis of N-(furan-2-ylmethyl)-4-(trifluoromethyl)aniline (16)

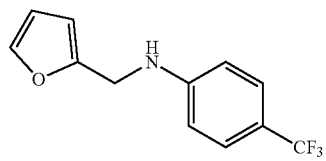 [SMILES: FC(F)(F)c1ccc(NCc2ccco2)cc1]

General Procedure B was followed using 4-bromobenzotrifluoride as the aryl halide, and furfurylamine as the amine. The reaction was run at room temperature for 15 hours. Purification was done by flash chromatography on silica gel, eluting with a gradient of 0-20% EtOAc/hexanes to give the product as a pale yellow solid (27.3 mg, 28%). NMR data matched previously reported spectra.[35,36] $^1$H NMR (400 MHz, Chloroform-d) δ 7.42 (d, J=8.5 Hz, 2H), 7.39-7.36 (m, 1H), 6.68 (d, J=8.5 Hz, 2H), 6.34 (dd, J=3.3, 1.9 Hz, 1H), 6.25 (d, J=3.2 Hz, 1H), 4.36 (s, 3H). $^{13}$C NMR (101 MHz, Chloroform-d) δ 151.9, 150.1, 142.3, 126.7 (q, $J_{C-F}$=3.8 Hz), 125.0 (q, $J_{C-F}$=271.4 Hz), 119.6 (q, $J_{C-F}$=32.6 Hz), 112.3, 110.6, 107.5, 41.0. $^{19}$F NMR (376 MHz, Chloroform-d) δ -61.1 (s, 3F). HRMS (DART-TOF): calculated for $C_{12}H_{11}F_3NO$ ([M+H]$^+$) 242.0787, found 242.0776.

Synthesis of N-(4-(trifluoromethyl)phenyl)pyridin-3-amine (17)

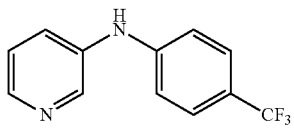 [SMILES: FC(F)(F)c1ccc(Nc2cccnc2)cc1]

General Procedure B was followed using 4-bromobenzotrifluoride as the aryl halide, and 3-aminopyridine as the amine. The reaction was run at room temperature for 15 hours. Purification was done by flash chromatography on silica gel, eluting with a gradient of 0-100% EtOAc/hexanes to give the product as a pale yellow solid (85.8 mg, 90%). NMR data matched previously reported spectra.[40] $^1$H NMR (400 MHz, DMSO-d$_6$) δ 8.85 (s, 1H), 8.44 (s, 1H), 8.17 (d, J=6.4, 1H), 7.64-7.58 (m, 1H), 7.55 (d, J=8.4 Hz, 2H), 7.32 (dd, J=8.3, 4.7 Hz, 1H), 7.17 (d, J=8.4 Hz, 2H). $^{13}$C NMR (101 MHz, DMSO-d$_6$) δ 147.2, 142.9, 141.5, 138.7, 127.1 (q, $J_{C-F}$=3.8 Hz), 125.5, 125.2 (q, $J_{C-F}$=271.8 Hz), 124.40, 119.8 (q, $J_{C-F}$=32.3 Hz), 115.5. $^{19}$F NMR (376 MHz, DMSO-d$_6$) δ -59.7 (s, 3F). HRMS (DART-TOF): calculated for $C_{12}H_{10}F_3N_2$ ([M+H]$^+$) 239.0791, found 239.0792.

Synthesis of 4-(3-(trifluoromethyl)phenyl)morpholine (18)

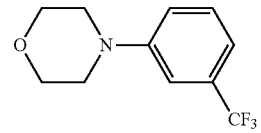 [SMILES: FC(F)(F)c1cccc(N2CCOCC2)c1]

General Procedure A was followed using 3-bromobenzotrifluoride as the aryl halide, and morpholine as the amine. The reaction was run at room temperature for 15 hours. Purification was done by flash chromatography on silica gel, eluting with a gradient of 0-15% EtOAc/hexanes to give the product as a pale yellow oil solid (52.7 mg, 57%). NMR data matched previously reported spectra.[41] $^1$H NMR (400 MHz, Chloroform-d) δ 7.42-7.29 (m, 1H), 7.16-7.08 (m, 2H), 7.08-7.03 (m, 1H), 3.88 (t, J=4.8, 4H), 3.21 (t, J=4.8, 4H). $^{13}$C NMR (101 MHz, Chloroform-d) δ 151.5, 131 0.7 (q, $J_{C-F}$=31 0.8 Hz), 129.8, 124.4 (q, $J_{C-F}$=273.4 Hz), 118.6, 116.4 (q, $J_{C-F}$=3.8 Hz), 112.0 (q, $J_{C-F}$=3.9 Hz), 66.9, 49.0. $^{19}$F NMR (376 MHz, Chloroform-d) δ -62.8 (s, 3F). HRMS (DART-TOF): calculated for $C_{11}H_{13}F_3NO$ ([M+H]$^+$) 232.0944, found 232.0934.

Synthesis of tert-butyl 4-(3-(trifluoromethyl)phenyl)piperazine-1-carboxylate (19)

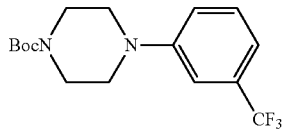 [SMILES: CC(C)(C)OC(=O)N1CCN(c2cccc(C(F)(F)F)c2)CC1]

General Procedure B was followed using 3-bromobenzotrifluoride as the aryl halide, and tert-butyl piperazine-1-carboxylate as the amine. The reaction was run at room temperature for 3 hours. Purification was done by flash chromatography on silica gel, eluting with a gradient of 0-15% EtOAc/hexanes to give the product as a pale yellow oil (79.3 mg, 60%). NMR data matched previously reported spectra.[42] $^1$H NMR (400 MHz, Chloroform-d) δ 7.40-7.31 (m, 1H), 7.13-7.08 (m, 2H), 7.08-7.02 (m, 1H), 3.60 (t, J=5.2, 4H), 3.18 (t, J=5.2, 4H), 1.49 (s, 9H). $^{13}$C NMR (101 MHz, Chloroform-d) δ 154.8, 151.5, 131.6 (q, $J_{C-F}$=31.8 Hz), 129.8, 124.4 (q, $J_{C-F}$=273.5 Hz), 119.4, 116.5 (q, $J_{C-F}$=3.9 Hz), 112.8 (q, $J_{C-F}$=3.9 Hz), 80.2, 49.0, 28.5. $^{19}$F NMR (376 MHz, Chloroform-d) δ −62.8 (s, 3F). HRMS (DART-TOF): calculated for $C_{16}H_{22}F_3N_2O_2$ ([M+H]$^+$) 331.1628, found 331.1632.

Synthesis of 1-(3-(trifluoromethyl)phenyl)piperidine (20)

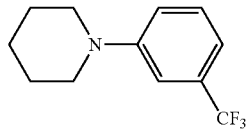 [SMILES: FC(F)(F)c1cccc(N2CCCCC2)c1]

General Procedure A was followed using 3-bromobenzotrifluoride as the aryl halide, and piperidine as the amine. The reaction was run at room temperature for 3 hours. Purification was done by flash chromatography on silica gel, eluting with a gradient of 0-10% EtOAc/hexanes to give the product as a pale yellow oil (33.0 mg, 36%). NMR data matched previously reported spectra.[43] $^1$H NMR (400 MHz, Chloroform-d) δ 7.32 (t, J=8.0 Hz, 1H), 7.12 (s, 1H), 7.10-6.99 (m, 2H), 3.21 (t, J=5.2, 4H), 1.76-1.67 (m, 4H), 1.66-1.57 (m, 2H). $^{13}$C NMR (101 MHz, Chloroform-d) δ 152.3, 131.4 (q, $J_{C-F}$=31.6 Hz), 129.5, 124.6 (q, $J_{C-F}$=273.5 Hz), 119.2, 115.3 (q, $J_{C-F}$=3.9 Hz), 112.6 (q, $J_{C-F}$=3.9 Hz), 50.3, 25.8, 24.3. $^{19}$F NMR (376 MHz, Chloroform-d) δ −62.7 (s, 3F). HRMS (DART-TOF): calculated for $C_{12}H_{15}F_3N$ ([M+H]$^+$) 230.1151, found 230.1151.

Synthesis of 4-(3,5-difluorophenyl)morpholine (21)

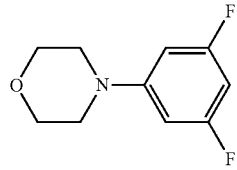 [SMILES: Fc1cc(F)cc(N2CCOCC2)c1]

General Procedure A was followed using 1-bromo-3,5-difluorobenzene as the aryl halide, and morpholine as the amine. The reaction was run at room temperature for 3 hours. Purification was done by flash chromatography on silica gel, eluting with a gradient of 0-15% EtOAc/hexanes to give the product as a white solid (56.3 mg, 71%). NMR data matched previously reported spectra.[44] $^1$H NMR (400 MHz, Chloroform-d) δ 6.42-6.23 (m, 3H), 3.83 (t, J=4.8 Hz, 4H), 3.14 (t, J=4.8 Hz, 4H). $^{13}$C NMR (101 MHz, Chloroform-d) δ 164.1 (dd, J=245.4, J=16.2 Hz), 153.4 (t, J=12.2 Hz), 98.0-97.8 (m), 94.6 (t, J=26.3 Hz), 66.7, 48.4. $^{19}$F NMR (376 MHz, Chloroform-d) δ −109.7-−109.9 (m, 2F). HRMS (DART-TOF): calculated for $C_{10}H_{12}F_2NO$ ([M+H]$^+$) 200.0881, found 200.0874.

Synthesis of tert-butyl 4-(3,5-difluorophenyl)piperazine-1-carboxylate (22)

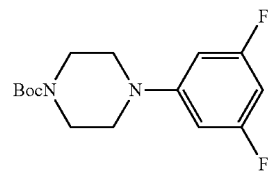 [SMILES: CC(C)(C)OC(=O)N1CCN(c2cc(F)cc(F)c2)CC1]

General Procedure B was followed using 1-bromo-3,5-difluorobenzene as the aryl halide, and tert-butyl piperazine-1-carboxylate as the amine. The reaction was run at room temperature for 3 hours. Purification was done by flash chromatography on silica gel, eluting with a gradient of 0-15% EtOAc/hexanes to give the product as a white solid (73.4 mg, 62%). $^1$H NMR (400 MHz, Chloroform-d) δ 6.40-6.30 (m, 2H), 6.27 (tt, J=8.8, 2.2 Hz, 1H), 3.55 (t, J=5.2, 4H), 3.14 (t, J=5.2, 4H), 1.48 (s, 9H). $^{13}$C NMR (101 MHz, Chloroform-d) δ 164.1 (dd, J=245.4, J=15.8 Hz), 154.7, 153.2 (t, J=12.3 Hz), 98.7-98.3 (m), 94.7 (t, J=23.3 Hz), 80.3, 48.3, 28.5. $^{19}$F NMR (376 MHz, Chloroform-d) δ −109.6-−109.8 (m, 2F). HRMS (DART-TOF): calculated for $C_{15}H_{21}F_2N_2O_2$ ([M+H]$^+$) 299.1556, found 299.1556.

Synthesis of N-(3,5-difluorophenyl)pyridin-3-amine (23)

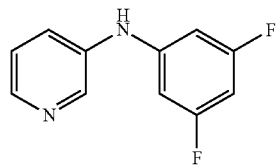 [SMILES: Fc1cc(F)cc(Nc2cccnc2)c1]

General Procedure B was followed using 1-bromo-3,5-difluorobenzene as the aryl halide, and 3-aminopyridine as the amine. The reaction was run at room temperature for 15 hours. Purification was done by flash chromatography on silica gel, eluting with a gradient of 0-100% EtOAc/hexanes to give the product as a white solid (74.4 mg, 90%). $^1$H NMR (400 MHz, DMSO-d$_6$) δ 8.81 (s, 1H), 8.39 (d, J=2.7 Hz, 1H), 8.26-8.07 (m, 1H), 7.68-7.48 (m, 1H), 7.41-7.21 (m, 1H), 6.83-6.48 (m, 3H). $^{13}$C NMR (101 MHz, DMSO-d$_6$) δ 163.4 (dd, J=243.8, J=16.3 Hz), 146.2 (t, J=13.5 Hz), 142.6, 141.1, 138.1, 125.1, 124.0, 98.5-98.0 (m), 94.5 (t, J=26.7 Hz). $^{19}$F NMR (376 MHz, DMSO-d$_6$) δ −109.5 (t, J=9.3 Hz, 2F). HRMS (DART-TOF): calculated for $C_{11}H_9F_2N_2$ ([M+H]$^+$) 207.0728, found 207.0730.

Synthesis of 4-(4-fluorophenyl)morpholine (24)

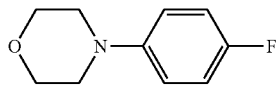

General Procedure B was followed using 1-bromo-4-fluorobenzene as the aryl halide, and morpholine as the amine. The reaction was run at room temperature for 15 hours. Purification was done by flash chromatography on silica gel, eluting with a gradient of 0-15% EtOAc/hexanes to give the product as a colorless oil (27.3 mg, 38%). NMR data matched previously reported spectra.[45] $^1$H NMR (400 MHz, Chloroform-d) δ 7.04-6.92 (m, 2H), 6.92-6.82 (m, 2H), 3.87 (t, J=4.8 Hz, 4H), 3.09 (t, J=4.8 Hz, 4H). $^{13}$C NMR (101 MHz, Chloroform-d) δ 157.5 (d, $J_{C-F}$=240.3 Hz), 148.1, 117.6 (d, $J_{C-F}$=7.8 Hz), 115.8 (d, $J_{C-F}$=22.2 Hz), 67.1, 50.5. $^{19}$F NMR (376 MHz, Chloroform-d) δ −124.2-−124.3 (m, 1F). HRMS (DART-TOF): calculated for $C_{10}H_{13}FNO$ ([M+H]+) 182.0976, found 182.0976.

Synthesis of 4-(3-chlorophenyl)morpholine (25)

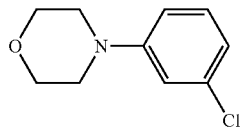 [SMILES: Clc1cccc(N2CCOCC2)c1]

General Procedure A was followed using 1-bromo-3-chlorobenzene as the aryl halide, and morpholine as the amine. The reaction was run at room temperature for 15 hours. Purification was done by flash chromatography on silica gel, eluting with a gradient of 0-15% EtOAc/hexanes to give the product as a colorless oil (65.4 mg, 83%). NMR data matched previously reported spectra.[46] $^1$H NMR (400 MHz, Chloroform-d) δ 7.18 (t, J=8.1 Hz, 1H), 6.89-6.81 (m, 2H), 6.80-6.74 (m, 1H), 3.85 (t, J=4.8 Hz, 4H), 3.15 (t, J=5.2 Hz, 4H). $^{13}$C NMR (101 MHz, Chloroform-d) δ 152.5, 135.2, 130.2, 119.8, 115.6, 113.7, 66.9, 49.0. HRMS (ESI-TOF): calculated for $C_{10}H_{13}ClNO$ ([M+H]$^+$) 198.0680, found 198.0691.

Synthesis of 4-morpholinobenzamide (26)

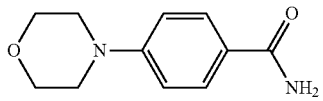

General Procedure A was followed using 4-bromobenzamide as the aryl halide, and morpholine as the amine. The reaction was run at room temperature for 15 hours. Purification was done by flash chromatography on silica gel, eluting with a gradient of 0-10% MeOH/DCM to give the product as a white solid (22.5 mg, 27%). NMR data matched previously reported spectra.[47] $^1$H NMR (400 MHz, DMSO-d$_6$) δ 7.88-7.64 (m, 3H), 7.09-6.83 (m, 3H), 3.74 (t, J=4.8 Hz, 4H), 3.21 (t, J=4.8 Hz, 4H). $^{13}$C NMR (101 MHz, DMSO-d$_6$) δ 167.5, 152.9, 128.8, 123.9, 113.3, 65.9, 47.4. HRMS (ESI-TOF): calculated for $C_{11}H_{15}N_2O_2$ ([M+H]$^+$) 207.1128, found 207.1121.

Synthesis of 4-phenylmorpholine (27)

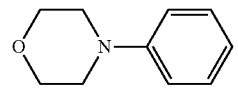 [SMILES: c1ccc(N2CCOCC2)cc1]

General Procedure A was followed using 4-bromobenzene as the aryl halide, and morpholine as the amine. The reaction was run at room temperature for 15 hours. Purification was done by flash chromatography on silica gel, eluting with a gradient of 0-15% EtOAc/hexanes to give the product as a white solid (34.8 mg, 53%). NMR data matched previously reported spectra.[46] $^1$H NMR (400 MHz, Chloroform-d) δ 7.35-7.26 (m, 2H), 6.99-6.83 (m, 3H), 3.87 (t, J=4.8 Hz, 4H), 3.17 (t, J=4.8 Hz, 4H). $^{13}$C NMR (101 MHz, Chloroform-d) δ 151.4, 129.3, 120.2, 115.8, 67.1, 49.5. HRMS (DART-TOF): calculated for $C_{10}H_{14}NO$ ([M+H]$^+$) 164.1070, found 164.1075.

Synthesis of 4-(p-tolyl)morpholine (28)

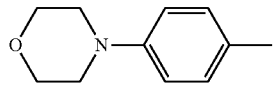

General Procedure A was followed using 4-bromotoluene as the aryl halide, and morpholine as the amine. The reaction was run at room temperature for 15 hours. Purification was done by flash chromatography on silica gel, eluting with a gradient of 0-15% EtOAc/hexanes to give the product as a white solid (23.4 mg, 33%). NMR data matched previously reported spectra.[46] $^1$H NMR (400 MHz, Chloroform-d) δ 7.14-7.05 (m, 2H), 6.88-6.80 (m, 2H), 3.87 (t, J=4.8 Hz, 4H), 3.11 (t, J=4.8 Hz, 4H), 2.28 (s, 3H). $^{13}$C NMR (101 MHz, Chloroform-d) δ 149.3, 129.8, 129.7, 116.2, 67.1, 50.1, 20.6. HRMS (DART-TOF): calculated for $C_{11}H_{16}NO$ ([M+H]$^+$) 178.1226, found 178.1225.

Synthesis of 4-(4-methoxyphenyl)morpholine (29)

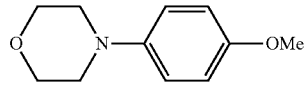 [SMILES: COc1ccc(N2CCOCC2)cc1]

General Procedure A was followed using 4-bromoanisole as the aryl halide, and morpholine as the amine. The reaction was run at room temperature for 15 hours. Purification was done by flash chromatography on silica gel, eluting with a gradient of 0-15% EtOAc/hexanes to give the product as a white solid (5.6 mg, 7%). NMR data matched previously reported spectra.[46] $^1$H NMR (400 MHz, Chloroform-d) δ 6.94-6.81 (m, 4H), 3.86 (t, J=4.4 Hz, 4H), 3.77 (s, 3H), 3.06 (t, J=4.8 Hz, 4H). $^{13}$C NMR (101 MHz, Chloroform-d) δ 154.2, 145.8, 118.0, 114.7, 67.2, 55.7, 51.0. HRMS (DART-TOF): calculated for $C_{11}H_{16}NO_2$ ([M+H]$^+$) 194.1176, found 194.1174.

Synthesis of 4-(3-methoxyphenyl)morpholine (30)

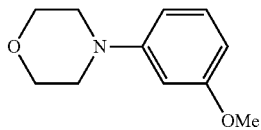 [SMILES: COc1cccc(N2CCOCC2)c1]

General Procedure A was followed using 3-bromoanisole as the aryl halide, and morpholine as the amine. The reaction was run at room temperature for 15 hours. Purification was done by flash chromatography on silica gel, eluting with a gradient of 0-15% EtOAc/hexanes to give the product as a colorless oil (45.8 mg, 59%). NMR data matched previously reported spectra.[46] $^1$H NMR (400 MHz, Chloroform-d) δ 7.24-7.14 (m, 1H), 6.57-6.50 (m, 1H), 6.48-6.41 (m, 2H), 3.85 (t, J=4.8 Hz, 4H), 3.80 (s, 3H), 3.16 (t, J=4.8 Hz, 4H). $^{13}$C NMR (101 MHz, Chloroform-d) δ 160.8, 152.8, 123.0, 108.6, 104.9, 102.4, 67.0, 55.3, 49.4. HRMS (DART-TOF): calculated for $C_{11}H_{16}NO_2$ ([M+H]$^+$) 194.1176, found 194.1181.

Synthesis of 4-(3,5-dimethoxyphenyl)morpholine (31)

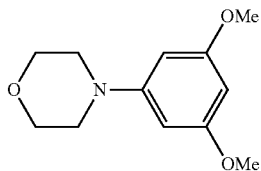 [SMILES: COc1cc(OC)cc(N2CCOCC2)c1]

General Procedure A was followed using 1-bromo-3,5-dimethoxybenzene as the aryl halide, and morpholine as the amine. The reaction was run at room temperature for 15 hours. Purification was done by flash chromatography on silica gel, eluting with a gradient of 0-15% EtOAc/hexanes to give the product as a white solid (47.4 mg, 53%). NMR data matched previously reported spectra.[48] $^1$H NMR (400 MHz, Chloroform-d) δ 6.08 (d, J=2.1 Hz, 2H), 6.04 (t, J=2.1 Hz, 1H), 3.84 (t, J=4.8 Hz, 4H), 3.78 (s, 6H), 3.14 (t, J=4.8 Hz, 4H). $^{13}$C NMR (101 MHz, Chloroform-d) δ 161.7, 153.4, 94.9, 92.0, 67.0, 55.4, 49.5. HRMS (DART-TOF): calculated for $C_{12}H_{18}NO_3$ ([M+H]$^+$) 224.1281, found 224.1281.

Synthesis of 4-morpholinobenzonitrile (32)

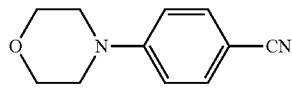 [SMILES: N#Cc1ccc(N2CCOCC2)cc1]

General Procedure A was followed using 4-bromobenzonitrile as the aryl halide, and morpholine as the amine. The reaction was run at room temperature for 3 hours. Purification was done by flash chromatography on silica gel, eluting with a gradient of 0-30% EtOAc/hexanes to give the product as a white solid (64.5 mg, 86%). NMR data matched previously reported spectra.[49] $^1$H NMR (400 MHz, Chloroform-d) b 7.54-7.45 (m, 2H), 6.89-6.81 (m, 2H), 3.83 (t, J=5.2 Hz, 4H), 3.27 (t, J=5.2 Hz, 4H). $^{13}$C NMR (101 MHz, Chloroform-d) δ 153.6, 133.6, 120.0, 114.1, 101.0, 66.5, 47.4. HRMS (DART-TOF): calculated for $C_{11}H_{13}N_2O$ ([M+H]$^+$) 189.1022, found 189.1011.

Synthesis of methyl 4-morpholinobenzoate (33)

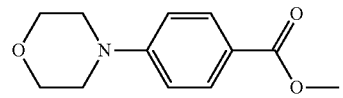 [SMILES: COC(=O)c1ccc(N2CCOCC2)cc1]

General Procedure A was followed using methyl 4-bromobenzoate as the aryl halide, and morpholine as the amine. The reaction was run at room temperature for 15 hours. Purification was done by flash chromatography on silica gel, eluting with a gradient of 0-30% EtOAc/hexanes to give the product as a white solid (57.7 mg, 65%). NMR data matched previously reported spectra.[50] $^1$H NMR (400 MHz, Chloroform-d) δ 7.95-7.91 (m, 2H), 6.89-6.81 (m, 2H), 3.88-3.80 (m, 7H), 3.27 (t, J=4.8 Hz, 4H). $^{13}$C NMR (101 MHz, Chloroform-d) δ 167.1, 154.3, 131.3, 120.4, 113.6, 66.7, 51.8, 47.8. HRMS (DART-TOF): calculated for $C_{12}H_{16}NO_3$ ([M+H]$^+$) 222.1125, found 222.1121.

Synthesis of 1-(4-morpholinophenyl)ethan-1-one (34)

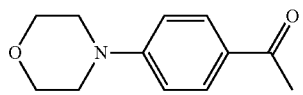

General Procedure A was followed using 4'-bromoacetophenone as the aryl halide, and morpholine as the amine. The reaction was run at room temperature for 15 hours. Purification was done by flash chromatography on silica gel, eluting with a gradient of 0-30% EtOAc/hexanes to give the product as a pale yellow solid (34.4 mg, 42%). NMR data matched previously reported spectra.[51] $^1$H NMR (400 MHz, Chloroform-d) δ 7.88 (d, J=8.8 Hz, 2H), 6.86 (d, J=8.8 Hz, 2H), 3.85 (t, J=4.8 Hz, 4H), 3.30 (t, J=5.2 Hz, 4H), 2.52 (s, 3H). $^{13}$C NMR (101 MHz, Chloroform-d) b 196.6, 154.3, 130.5, 128.3, 113.4, 66.7, 47.7, 26.3. HRMS (DART-TOF): calculated for $C_{12}H_{16}NO_2$ ([M+H]$^+$) 206.1176, found 206.1177.

Synthesis of 4-(pyridin-3-yl)morpholine (35)

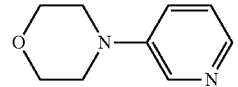 [SMILES: c1cncc(N2CCOCC2)c1]

General Procedure B was followed using 3-bromopyridine as the aryl halide, and morpholine as the amine. The reaction was run at room temperature for 15 hours. Purification was done by flash chromatography on silica gel, eluting with a gradient of 0-100% EtOAc/hexanes to give the product as a pale yellow oil (23.4 mg, 36%). NMR data matched previously reported spectra.[46] $^1$H NMR (400 MHz, Chloroform-d) δ 8.30 (s, 1H), 8.12 (t, J=2.8 Hz, 1H), 7.18-7.14 (m, 2H), 3.86 (t, J=4.8 Hz, 4H), 3.18 (t, J=4.8 Hz, 4H). $^{13}$C NMR (101 MHz, Chloroform-d) δ 147.0, 141.3, 138.5, 123.6, 122.2, 66.8, 48.7. HRMS (DART-TOF): calculated for $C_9H_{13}N_2O$ ([M+H]$^+$) 165.1022, found 165.1018.

Synthesis of 4-(pyrimidin-5-yl)morpholine (36)

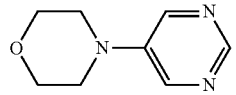 [SMILES: c1ncc(N2CCOCC2)cn1]

General Procedure B was followed using 5-bromopyrimidine as the aryl halide, and morpholine as the amine. The reaction was run at room temperature for 15 hours. Purification was done by flash chromatography on silica gel, eluting with a gradient of 0-100% EtOAc/hexanes to give the product as a pale yellow oil (13.8 mg, 21%). NMR data matched previously reported spectra.[52] $^1$H NMR (400 MHz, Chloroform-d) δ 8.73 (s, 1H), 8.36 (s, 2H), 3.89 (t, J=5.6 Hz, 4H), 3.23 (t, J=4.8 Hz, 4H). $^{13}$C NMR (101 MHz, Chloroform-d) δ 150.3, 144.3, 143.6, 66.5, 47.6. HRMS (DART-TOF): calculated for $C_8H_{12}N_3O$ ([M+H]$^+$) 166.0975, found 166.0965.

Synthesis of 1-(4-((3-bromophenyl)thio)phenyl)ethan-1-one (37)

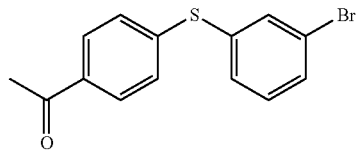 [SMILES: CC(=O)c1ccc(Sc2cccc(Br)c2)cc1]

A 50 mL storage flask was charged with a stir bar, flame dried under vacuum and back filled with nitrogen three times. The flask was then charged with $Cs_2CO_3$ (1.466 g, 4.5 mmol, 1.5 equiv.), 4'-bromoacetophenone (0.597 g, 3.0 mmol, 1.00 equiv.), 3-bromothiophenol (0.851 g, 4.5 mmol, 1.5 equiv.) and 23 mL DMSO. The reaction mixture was evacuated and purged with inert gas ($N_2$) three times. The reaction mixture was then placed into an LED-lined beaker along with a tube for air cooling and stirred. After stirring for 12 hours, the reaction mixture was washed with water, extracted with EtOAc, and concentrated under vacuum. The product was isolated by flash chromatography (1:5 EtOAc: hexanes) as a white solid (0.516 g, 56%). $^1$H NMR (400 MHz, Chloroform-d) δ 7.89-7.76 (m, 2H), 7.58 (t, J=1.8 Hz, 1H), 7.53-7.43 (m, 1H), 7.40-7.32 (m, 1H), 7.31-7.20 (m, 3H), 2.56 (s, 3H). $^{13}$C NMR (101 MHz, Chloroform-d) δ 197.1, 143.1, 135.4, 135.4, 135.3, 131.6, 131.5, 131.0, 129.2, 128.8, 123.4, 26.6. HRMS (ESI-TOF): calculated for $C_{14}H_{12}BrOS$ ([M+H]$^+$) 306.9787, found 306.9813.

Synthesis of 1-(4-((3-(pyridin-3-ylamino)phenyl)thio)phenyl)ethan-1-one (38)

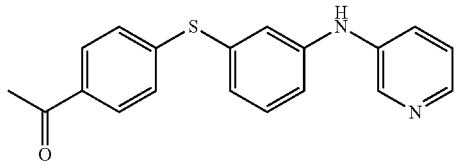 [SMILES: CC(=O)c1ccc(Sc2cccc(Nc3cccnc3)c2)cc1]

General Procedure B was followed using 1-(4-((3-bromophenyl)thio)phenyl)ethan-1-one (37) as the aryl halide, and 3-aminopyridine as the amine. The reaction was run at room temperature for 15 hours. Purification was done by flash chromatography on silica gel, eluting with a gradient of 0-80% EtOAc/hexanes to give the product as a pale yellow solid (113.4 mg, 88%). $^1$H NMR (400 MHz, Chloroform-d) δ 8.39 (d, J=2.8 Hz, 1H), 8.20 (d, J=4.4, 1H), 7.88-7.80 (m, 2H), 7.45-7.38 (m, 1H), 7.32-7.26 (m, 3H), 7.20-7.12 (m, 2H), 7.10-7.02 (m, 2H), 6.06 (s, 1H), 2.56 (s, 3H). $^{13}$C NMR (101 MHz, Chloroform-d) δ 197.3, 144.3, 143.7, 142.9, 141.0, 139.0, 134.9, 134.0, 130.7, 129.1, 128.2, 126.3, 124.5, 123.9, 121.9, 117.6, 26.6. HRMS (ESI-TOF): calculated for $C_{19}H_{17}N_2OS$ ([M+H]$^+$) 321.1056, found 321.1063.

Synthesis of 1-(2-(4-(3-(trifluoromethyl)phenyl)piperazin-1-yl)ethyl)-1,3-dihydro-2H-benzo[d]imidazol-2-one (39, Flibanserin)

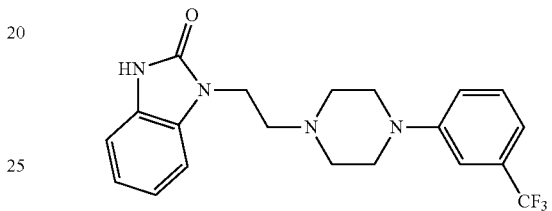

Using tert-butyl 4-(3-(trifluoromethyl)phenyl)piperazine-1-carboxylate (19) as the precursor, compound 39 was synthesized using previously published procedures.[19] NMR data matched previously reported spectra.[53] $^1$H NMR (400 MHz, Chloroform-d) δ 9.99 (s, 1H), 7.32 (t, J=8.0 Hz, 1H), 7.15-6.97 (m, 7H), 4.07 (t, J=6.8 Hz, 2H), 3.21 (t, J=4.8 Hz, 4H), 2.79 (t, J=6.9 Hz, 2H), 2.72 (t, J=5.2 Hz, 4H). $^{13}$C NMR (101 MHz, Chloroform-d) δ 155.8, 151.5, 131.6 (q, $J_{C-F}$=31.9 Hz), 130.5, 129.6, 128.2, 124.5 (q, $J_{C-F}$=273.5 Hz), 121.7, 121.4, 118.8, 115.9 (q, $J_{C-F}$=4.0 Hz), 112.2 (q, $J_{C-F}$=3.9 Hz), 109.8, 108.1, 55.9, 53.2, 48.8, 38.7. $^{19}$F NMR (376 MHz, Chloroform-d) δ −62.8 (s, 3F). HRMS (ESI-TOF): calculated for $C_{20}H_{21}F_3N_4O$ ([M+H]$^+$) 391.1740, found 391.1739.

Synthesis of 1-(2-(4-(4-(trifluoromethyl)phenyl)piperazin-1-yl)ethyl)-1,3-dihydro-2H-benzo[d]imidazol-2-one (40)

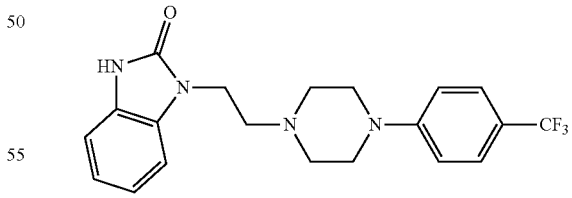

Using tert-butyl 4-(4-(trifluoromethyl)phenyl)piperazine-1-carboxylate (9) as the precursor, compound 40 was synthesized using previously published procedures.[53] $^1$H NMR (400 MHz, Chloroform-d) δ 10.02 (s, 1H), 7.45 (d, J=8.7 Hz, 2H), 7.20-6.99 (m, 4H), 6.87 (d, J=8.6 Hz, 2H), 4.07 (t, J=6.8 Hz, 2H), 3.24 (t, J=4.8 Hz, 4H), 2.78 (t, J=6.8 Hz, 2H), 2.71 (t, J=5.6 Hz, 4H). $^{13}$C NMR (101 MHz, Chloroform-d) δ 155.7, 153.4, 130.4, 128.0, 126.5 (q, $J_{C-F}$=4.4 Hz), 124.9 (q, $J_{C-F}$=271.4 Hz), 121.7, 121.4, 120.6 (q, $J_{C-F}$=32.9 Hz), 114.6, 109.7, 108.1, 55.8, 53.1, 48.1, 38.6. $^{19}$F NMR (376

MHz, Chloroform-d) δ −61.4 (s, 3F). HRMS (ESI-TOF): calculated for $C_{20}H_{21}F_3N_4O$ ([M+H]$^+$) 391.1740, found 391.1767.

Synthesis of 1-(2-(4-(3,5-difluorophenyl)piperazin-1-yl)ethyl)-1,3-dihydro-2H-benzo[d]imidazol-2-one (41)

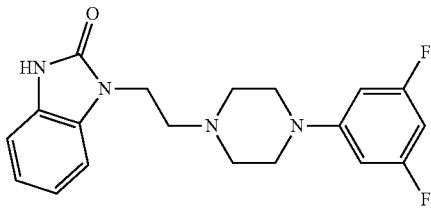 [SMILES: O=c1[nH]c2ccccc2n1CCN1CCN(c2cc(F)cc(F)c2)CC1]

Using tert-butyl 4-(3,5-difluorophenyl)piperazine-1-carboxylate (22) as the precursor, compound 41 was synthesized using previously published procedures.[53] $^1$H NMR (400 MHz, Chloroform-d) δ 10.25 (s, 1H), 7.17-6.94 (m, 4H), 6.37-6.27 (m, 2H), 6.23 (tt, J=8.9, 2.2 Hz, 1H), 4.06 (t, J=6.8 Hz, 2H), 3.16 (t, J=4.8 Hz, 4H), 2.77 (t, J=6.8 Hz, 2H), 2.69 (t, J=5.2 Hz, 4H). $^{13}$C NMR (101 MHz, Chloroform-d) δ 164.1 (dd, J=244.8, J=16.1 Hz), 155.9, 153.2 (t, J=12.3 Hz), 130.4, 128.2, 121.7, 121.4, 109.8, 108.0, 98.2-97.8 (m), 94.1 (t, J=26.2 Hz), 55.8, 53.0, 48.2, 38.7. $^{19}$F NMR (376 MHz, Chloroform-d) δ −110.0−−110.1 (m, 2F). HRMS (ESI-TOF): calculated for $C_{19}H_{21}F_2N_4O$ ([M+H]$^+$) 359.1678, found 359.1690.

Example 2—Mechanistic Study

Figure 12A:
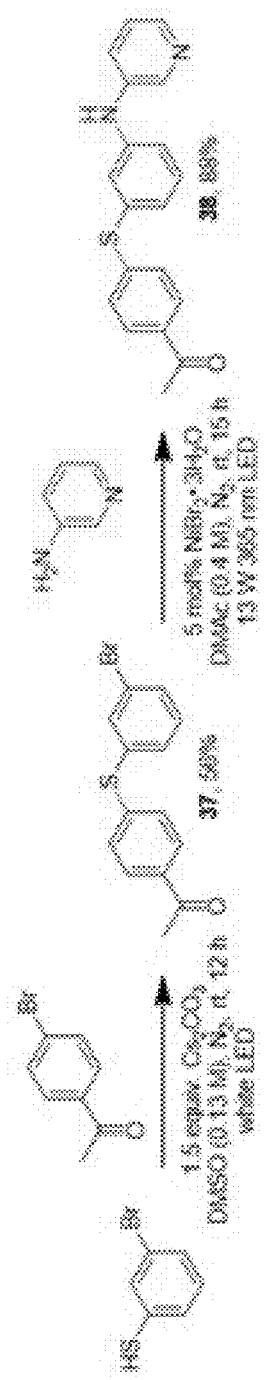
FIG. 12A and FIG. 12B depicts synthetic applications in accordance with embodiments of the disclosure.
Figure 12B:
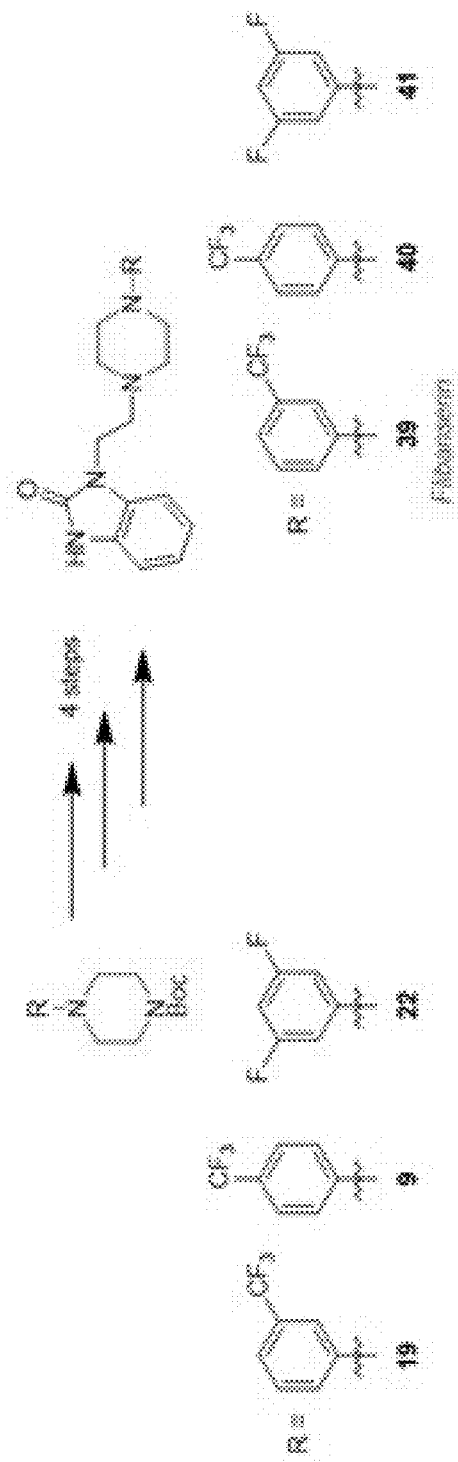

To further establish the utility of the C—N cross-coupling methodology of the disclosure, it was employed in multi-step syntheses (FIG. 12A and FIG. 12B). Recently, a visible light-driven aryl C—S cross-coupling methodology that proceeds under mild conditions to synthesize a wide range of aryl thioether products through white LED irradiation of a solution containing (hetero)aryl thiol, (hetero)aryl halide and $Cs_2CO_3$ in DMSO at room temperature in the absence of catalysts was reported.[30] Using this method, aryl thioether 37 was synthesized at 56% yield which was subsequently subjected to the C—N cross-coupling conditions described herein, coupling it with 3-aminopyridine, to yield 38 in 88% yield (FIG. 12A). This example highlights two industrially important processes, namely aryl C—S and C—N cross-couplings that can be driven by light irradiation under mild conditions to reach molecular complexity.

The piperazine functionality is abundant across pharmaceutical products (vide supra).[28] Using established methods,[31] in four synthetic steps aryl coupled piperazine derivatives 19, 9, and 22 were converted to flibanserin (39) and two flibanserin derivatives (40 and 41, FIG. 4B). It should be noted that 40 can also be accessed from 8, therefore eliminating both Boc protection and deprotection steps. These examples illuminate the prospect of efficient and sustainable access to medicinally relevant precursors using the C—N coupling methodology of the disclosure for the development and manufacturing of pharmaceutical products.

Figure 13A:
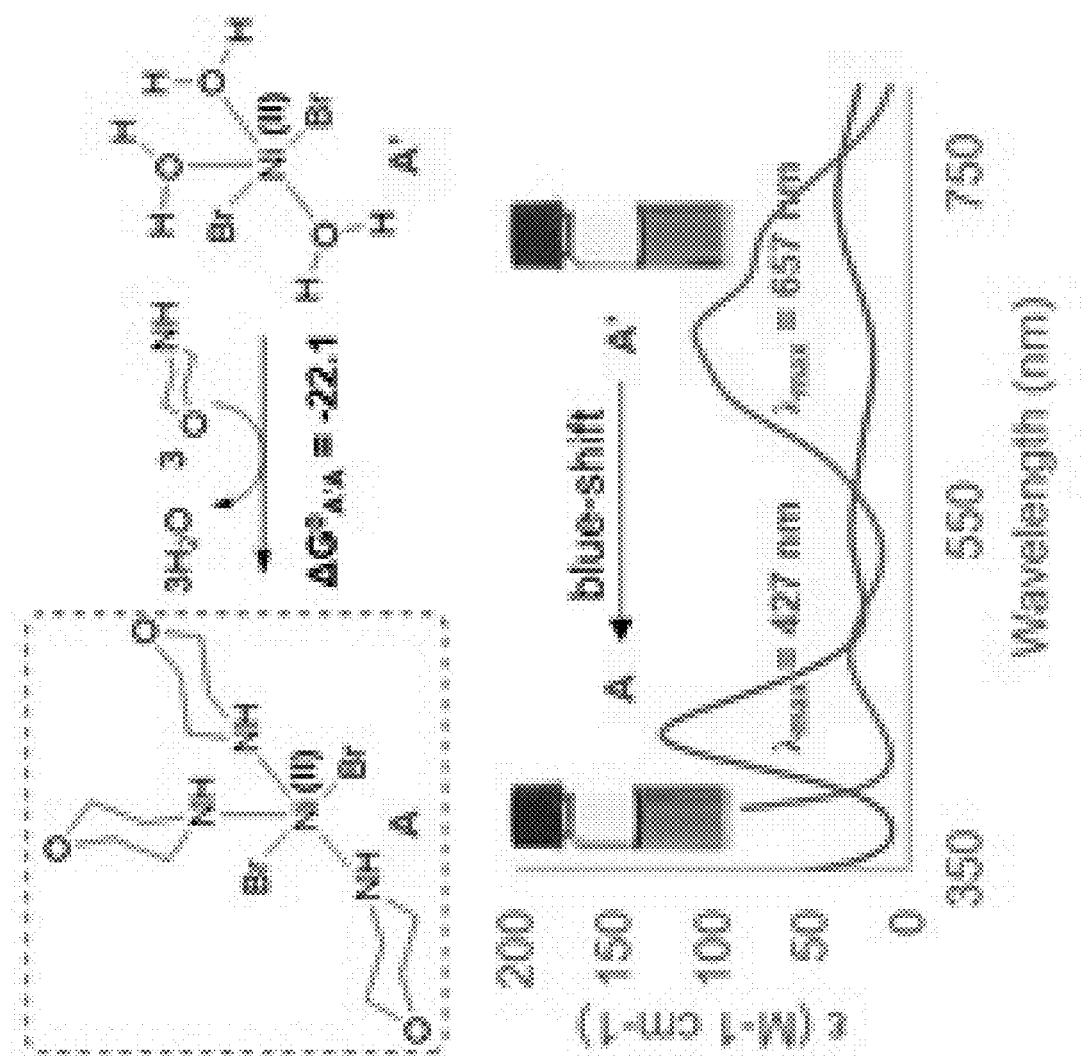
FIG. 13A, FIG. 13B, and FIG. 13C depict mechanistic studies in accordance with embodiments of the disclosure.

To gain insight into this mechanism, density functional theory (DFT) calculations were performed to compute the energetics of intermediates involved in the proposed lowest energy potential energy surface (FIG. 13A, FIG. 13B, and FIG. 13C).[32,33] Specifically, to construct possible mechanistic pathways, the mechanism to produce 1a was investigated. A proposed mechanism commences with a nickel-amine complex $NiBr_2.(morpholine)_3$ (complex A, FIG. 13A) as the characteristic teal color of $NiBr_2.3H_2O$ (complex A') solution in DMAc ($\lambda_{max}$=657 nm) significantly blue-shifted to brownish yellow ($\lambda_{max}$=427 nm) upon morpholine addition to generate the key complex A. The UV-vis spectra of A remained identical upon addition of 4-bromobenzotrifluoride and thus only A is responsible for photon absorption to initiate C—N cross coupling. Computationally, the displacement of three water molecules by three morpholine molecules to generate A was determined to be exergonic by 22.1 kcal/mol. In addition, the ground state of A was computationally determined to be triplet, which was 14.0 kcal/mol more stable than the corresponding singlet. Corroborating DFT predictions, A was previously isolated with a measured magnetic moment of 2.95 BM, reaffirming the triplet ground state of A.[34]

Figure 13B:
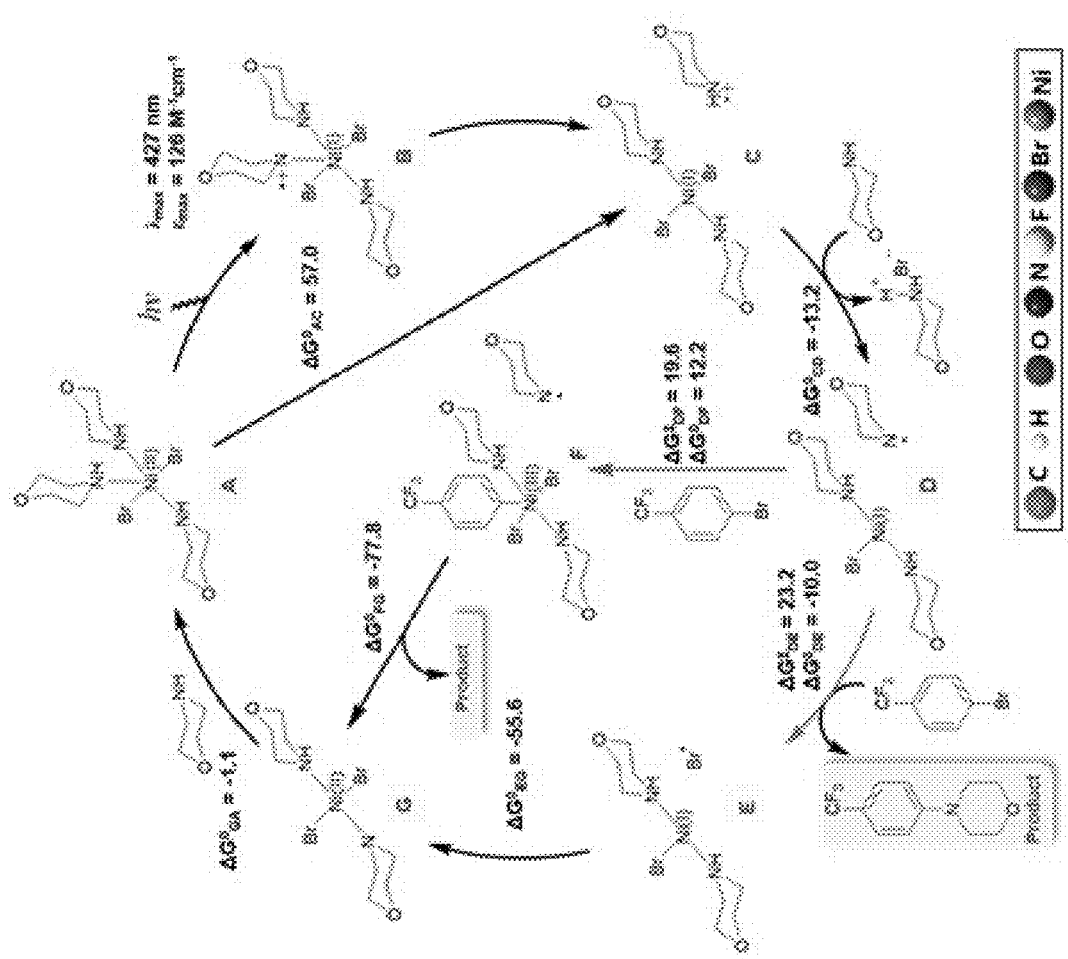
Figure 13C:
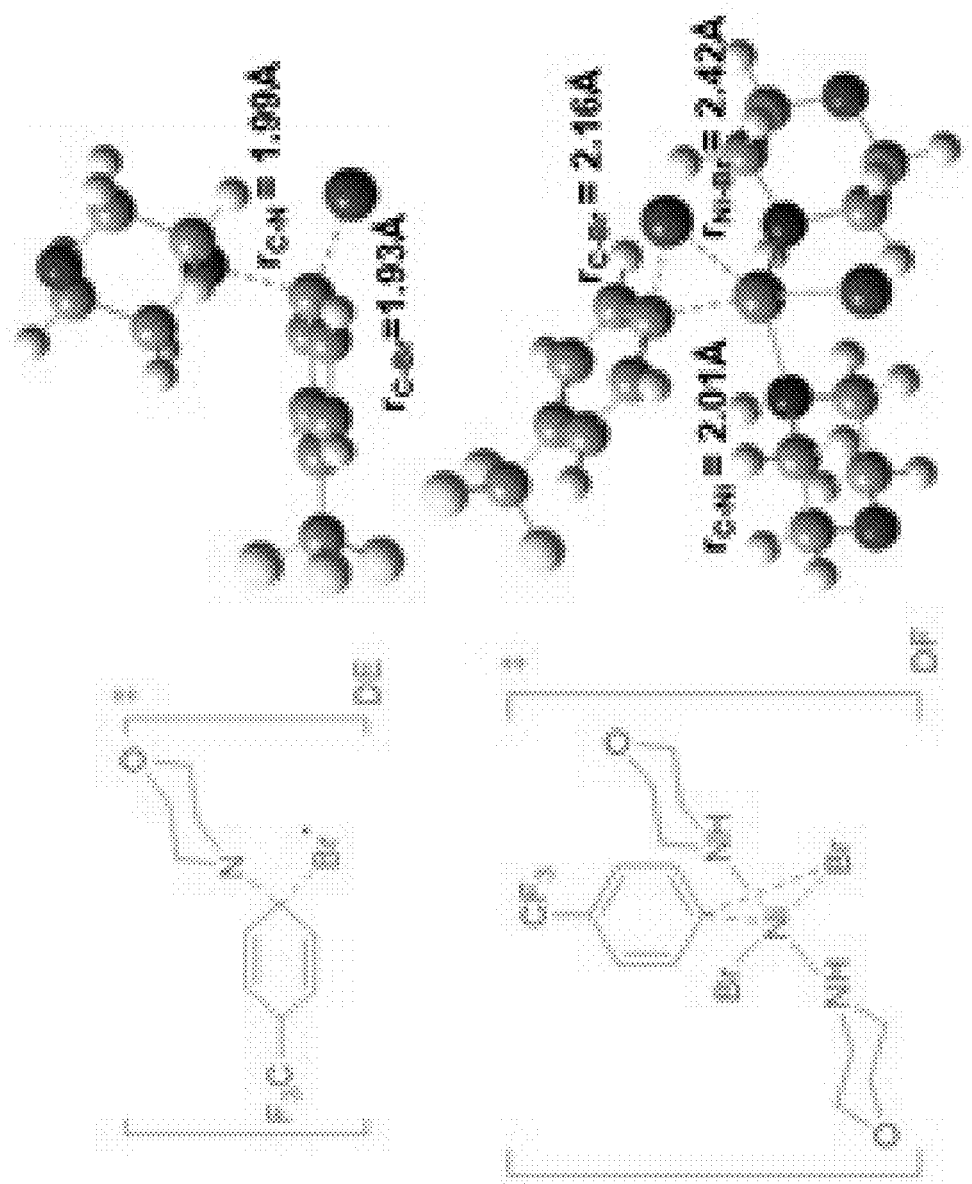

Without being bound by theory, it is proposed that the catalytic activity for aryl C—N bond formation begins with photon absorption by A ($\lambda_{max}$=427 nm, $\varepsilon_{max}$=126 M$^{-1}$cm$^{-1}$, FIG. 13B). Photoinduced electron transfer from electron-rich morpholine to the electron-poor Ni(II) metal center results in the reduced Ni(I) and oxidized morpholine radical cation (B), which can subsequently dissociate into the corresponding ion pairs (C). Thermodynamically, the free energy cost to produce C from A ($\Delta G^0_{AC}$) is endergonic by 57.0 kcal/mol, which is energetically supplied by photon absorption (427 nm or 67.0 kcal/mol). The proton of the morpholine radical cation is relatively acidic and the bromide anion of Ni(I) complex C is also comparatively labile such that excess morpholine in solution can act as a base to neutralize the HBr to form D ($\Delta G^0_{CD}$=−13.2 kcal/mol).

The Ni(I) species and morpholine radical in D are both reactive intermediates that can react with 4-bromobenzotrifluoride through either step DE or DF. In step DE, the morpholine radical adds to 4-bromobenzotrifluoride to form the desired product 1a through bromine atom displacement (E). The DFT-predicted free energy of activation ($\Delta G^\ddagger_{DE}$) for this step is 23.3 kcal/mol while the free energy of reaction is thermodynamically favored by 10.0 kcal/mol. The Ni(I) species and the bromine atom in E can then quench ($\Delta G^0_{EG}$=−55.6 kcal/mol) to form the closed-shell $NiBr_2.(morpholine)_2$ complex (G). G can then associate with morpholine in solution ($\Delta G^0_{GA}$=−1.1 kcal/mol) to re-enter the catalytic cycle as A. Alternatively, 4-bromobenzotrifluoride can oxidatively add to Ni(I) species in D to form a Ni(III) intermediate (F) ($\Delta G^\ddagger_{DF}$=19.6 kcal/mol and $\Delta G^0_{DF}$=12.2 kcal/mol). This Ni(III) and the morpholine radical can then react energetically ($\Delta G^0_{FG}$=−77.8 kcal/mol) to eliminate the C—N product 1a while forming the aforementioned G.

The description above includes example systems, methods, techniques, and/or instruction sequences that embody techniques of the present disclosure. However, it is understood that the described disclosure may be practiced without these specific details.

REFERENCES

1. Bariwal, J. & Van der Eycken, E. C—N bond forming cross-coupling reactions: an overview. *Chem. Soc. Rev.* 42, 9283-9303 (2013).
2. Ruiz-Castillo, P. & Buchwald, S. L. Applications of palladium-catalyzed C—N cross-coupling reactions. *Chem. Rev.* 116, 12564-12649 (2016).

3. Brown, D. G. & Boström, J. Analysis of past and present synthetic methodologies on medicinal chemistry: where have all the new reactions gone? *J. Med. Chem.* 59, 4443-4458, (2016).
4. Ullmann, F. Ueber eine neue Bildungsweise von Diphenylaminderivaten. *Ber. Dtsch. Chem. Ges.* 36, 2382-2384 (1903).
5. Monnier, F. & Taillefer, M. Catalytic C—C, C—N, and C—O Ullmann-type coupling reactions. *Angew. Chem. Int. Ed.* 48, 6954-6971 (2009).
6. Hartwig, J. F. Transition metal catalyzed synthesis of arylamines and aryl ethers from aryl halides and triflates: scope and mechanism. *Angew. Chem. Int. Ed.* 37, 2046-2067 (1998).
7. Wolfe, J. P. & Buchwald, S. L. Palladium-catalyzed amination of aryl iodides. *J. Org. Chem.* 61, 1133-1135 (1996).
8. Wolfe, J. P. & Buchwald, S. L. Nickel-catalyzed amination of aryl chlorides. *J. Am. Chem. Soc.* 119, 6054-6058 (1997).
9. Ramgren, S. D., Silberstein, A. L., Yang, Y. & Garg, N. K. Nickel-catalyzed amination of aryl sulfamates. *Angew. Chem. Int. Ed.* 50, 2171-2173 (2011).
10. Lavoie, C. M. et al. Challenging nickel-catalysed amine arylations enabled by tailored ancillary ligand design. *Nat. Commun.* 7, 11073, (2016).
11. Green, R. A. & Hartwig, J. F. Nickel-catalyzed amination of aryl chlorides with ammonia or ammonium salts. *Angew. Chem. Int. Ed.* 54, 3768-3772 (2015).
12. Marin, M., Rama, R. J. & Nicasio, M. C. Ni-catalyzed amination reactions: an overview. *Chem. Rec.* 16, 1819-1832 (2016).
13. Creutz, S. E., Lotito, K. J., Fu, G. C. & Peters, J. C. Photoinduced Ullmann C—N coupling: demonstrating the viability of a radical pathway. *Science* 338, 647-651, (2012).
14. Ziegler, D. T. et al. A versatile approach to Ullmann C—N couplings at room temperature: new families of nucleophiles and electrophiles for photoinduced, copper-catalyzed processes. *J. Am. Chem. Soc.* 135, 13107-13112 (2013).
15. Oderinde, M. S. et al. Highly chemoselective iridium photoredox and nickel catalysis for the cross-coupling of primary aryl amines with aryl halides. *Angew. Chem. Int. Ed.* 55, 13219-13223 (2016).
16. Corcoran, E. B. et al. Aryl amination using ligand-free Ni(II) salts and photoredox catalysis. *Science* 353, 279-283 (2016).
17. Theriot, J. C. et al. Organocatalyzed atom transfer radical polymerization driven by visible light. *Science* 352, 1082-1086 (2016).
18. Pearson, R. M., Lim, C.-H., McCarthy, B. G., Musgrave, C. B. & Miyake, G. M. Organocatalyzed atom transfer radical polymerization using N-aryl phenoxazines as photoredox patalysts. *J. Am. Chem. Soc.* 138, 11399-11407 (2016).
19. Du, Y. et al. Strongly reducing, visible-light organic photoredox catalysts as sustainable alternatives to precious metals. *Chem. Eur. J.* 23, 10962-10968 (2017).
20. Li, C. et al. Electrochemically enabled, nickel-catalyzed amination. *Angew. Chem. Int. Ed.* 56, 13088-13093 (2017).
21. Arias-Rotondo, D. M. & McCusker, J. K. The photophysics of photoredox catalysis: a roadmap for catalyst design. *Chem. Soc. Rev.* 45, 5803-5820 (2016).
22. Romero, N. A. & Nicewicz, D. A. Organic photoredox catalysis. *Chem. Rev.* 116, 10075-10166 (2016).
23. Twilton, J., Zhang, P., Shaw, M. H., Evans, R. W. & MacMillan, D. W. The merger of transition metal and photocatalysis. *Nat. Rev. Chem.* 1, (2017).
24. Ishida, N., Masuda, Y., Ishikawa, N. & Murakami, M. Cooperation of a nickel-bipyridine complex with light for benzylic C—H arylation of toluene derivatives. *Asian J. Org. Chem.* 6, 669-672, (2017).
25. Morris, S. A., Wang, J. & Zheng, N. The prowess of photogenerated amine radical cations in cascade reactions: from carbocycles to heterocycles. *Acc. Chem. Res.* 49, 1957-1968, (2016).
26. Xiong, T. & Zhang, Q. New amination strategies based on nitrogen-centered radical chemistry. *Chem. Soc. Rev.* 45, 3069-3087 (2016).
27. Tasker, S. Z., Standley, E. A. & Jamison, T. F. Recent advances in homogeneous nickel catalysis. *Nature* 509, 299-309 (2014).
28. Vitaku, E., Smith, D. T. & Njardarson, J. T. Analysis of the structural diversity, substitution patterns, and frequency of nitrogen heterocycles among U.S. FDA approved pharmaceuticals. *J. Med. Chem.* 57, 10257-10274 (2014).
29. Dean, B. V., Stellpflug, S. J., Burnett, A. M. & Engebretsen, K. M. 2C or not 2C: phenethylamine designer drug review. *J. Med. Toxicol.* 9, 172-178 (2013).
30. Liu, B., Lim, C.-H. & Miyake, G. M. Visible-light-promoted C—S cross-coupling via intermolecular charge transfer. *J. Am. Chem. Soc.* 139, 13616-13619 (2017).
31. Yang, F. et al. A facile route of synthesis for making Flibanserin. *Org. Process Res. Dev.* 20, 1576-1580, (2016).
32. Lim, C.-H., Holder, A. M., Hynes, J. T. & Musgrave, C. B. Reduction of CO2 to methanol catalyzed by a biomimetic organo-hydride produced from pyridine. *J. Am. Chem. Soc.* 136, 16081-16095 (2014).
33. Lim, C.-H. et al. Intramolecular charge transfer and ion pairing in N,N-diaryl dihydrophenazine photoredox catalysts for efficient organocatalyzed atom transfer radical polymerization. *J. Am. Chem. Soc.* 139, 348-355 (2017).
34. Palazón, J., Gálvez, J., Garcia, G. & Lopez, G. Some complexes of nickel (II) with morpholine. *Polyhedron* 2, 1353-1356 (1983).
35. Corcoran, E. B. et al. Aryl amination using ligand-free Ni(II) salts and photoredox catalysis. *Science* 353, 279-283 (2016).
36. Du, Y. et al. Strongly reducing, visible-light organic photoredox catalysts as sustainable alternatives to precious metals. *Chem. Eur. J.* 23, 10962-10968 (2017).
37. Li, C. et al. Electrochemically enabled, nickel-catalyzed amination. *Angew. Chem. Int. Ed.* 56, 13088-13093 (2017).
38. Reilly, S. W. & Mach, R. H. Pd-catalyzed synthesis of piperazine scaffolds under aerobic and solvent-free conditions. *Org. Lett.* 18, 5272-5275 (2016).
39. Lui, E. K. J. & Schafer, L. L. Facile synthesis and isolation of secondary amines via a sequential titanium (IV)-catalyzed hydroamination and palladium-catalyzed hydrogenation. *Adv. Synth. Catal.* 358, 713-718 (2016).
40. Mazu, T. K. et al. δ-Carbolines and their ring-opened analogs: Synthesis and evaluation against fungal and bacterial opportunistic pathogens. *Eur. J. Med. Chem.* 46, 2378-2385 (2011).
41. Li, J., Cui, M., Yu, A. & Wu, Y. Carbene adduct of cyclopalladated ferrocenylimine as an efficient catalyst for the amination of aryl chlorides. *J. Organomet. Chem.* 692, 3732-3742 (2007).

42. Yong, F.-F., Teo, Y.-C. & Tan, K.-N. Efficient copper-catalyzed cross-coupling of 1-Boc-piperazine with aryl iodides and its application in the synthesis of trazodone. *Tetrahedron Lett.* 54, 5332-5334 (2013).
43. Chen, M. & Buchwald, S. L. Rapid and efficient trifluoromethylation of aromatic and heteroaromatic compounds using potassium trifluoroacetate enabled by a flow system. *Angew. Chem. Int. Ed.* 52, 11628-11631 (2013).
44. Demory, E., Devaraj, K., Orthaber, A., Gates, P. J. & Pilarski, L. T. Boryl (hetero)aryne precursors as versatile arylation reagents: synthesis through C—H activation and orthogonal reactivity. *Angew. Chem. Int. Ed.* 54, 11765-11769 (2015).
45. Li, J. & Wang, Z.-X. Nickel-catalyzed amination of aryl 2-pyridyl ethers via cleavage of the carbon-oxygen bond. *Org. Lett.* 19, 3723-3726 (2017).
46. Guo, D., Huang, H., Xu, J., Jiang, H. & Liu, H. Efficient iron-catalyzed N-arylation of aryl halides with amines. *Org. Lett.* 10, 4513-4516 (2008).
47. Richardson, J., Ruble, J. C., Love, E. A. & Berritt, S. A method for identifying and developing functional group tolerant catalytic reactions: application to the Buchwald-Hartwig amination. *J. Org. Chem.* 82, 3741-3750 (2017).
48. Lü, B. et al. 2,6-Diisopropoxyphenyl(dicyclohexyl)phosphine: A new ligand for palladium-catalyzed amination reactions of aryl chlorides with potassium hydroxide as the base. *Adv. Synth. Catal.* 353, 100-112 (2011).
49. Reddy, C. V., Kingston, J. V. & Verkade, J. G. (t-Bu)2PNP(i-BuNCH2CH2)3N: New efficient ligand for palladium-catalyzed C—N couplings of aryl and heteroaryl bromides and chlorides and for vinyl bromides at room temperature. *J. Org. Chem.* 73, 3047-3062 (2008).
50. Mochizuki, A., Nagata, T., Kanno, H., Suzuki, M. & Ohta, T. 2-Aminomethylphenylamine as a novel scaffold for factor Xa inhibitor. *Bioorganic Med. Chem.* 19, 1623-1642 (2011).
51. Doherty, S. et al. Ortho,ortho-substituted KITPHOS monophosphines: highly efficient ligands for palladium-catalyzed C—C and C—N Bond Formation. *Adv. Synth. Catal.* 352, 201-211 (2010).
52. Charles, M. D., Schultz, P. & Buchwald, S. L. Efficient Pd-catalyzed amination of heteroaryl halides. *Org. Lett.* 7, 3965-3968 (2005).
53. Yang, F. et al. A facile route of synthesis for making Flibanserin. *Org. Process Res. Dev.* 20, 1576-1580 (2016).

All cited references are herein expressly incorporated by reference in their entirety.

Whereas particular embodiments have been described above for purposes of illustration, it will be appreciated by those skilled in the art that numerous variations of the details may be made without departing from the disclosure as described in the appended claims.

What is claimed is:

1. A method for forming an aryl carbon-nitrogen bond, the method comprising:
   contacting an aryl halide with an amine in the presence of a Ni(II) salt catalyst solution and an optional additional base, thereby forming a reaction mixture; and
   exposing the reaction mixture to light under reaction conditions sufficient to form the aryl carbon-nitrogen bond;
   wherein the formation of the aryl carbon-nitrogen bond is light-driven and Ni-catalyzed without the addition of a photoredox catalyst under said reaction conditions; wherein the light is at about 300 nm to 405 nm.

2. The method of claim 1, wherein the reactions conditions comprise holding the reaction mixture under light exposure at between about room temperature and about 80° C. for between about 1 hour and about 20 hours such that at least about 50% reaction yield is obtained.

3. The method of claim 2, wherein at least about 80% reaction yield is obtained.

4. The method of claim 1, wherein the aryl halide is selected from the group consisting of an aryl bromide, an aryl chloride, and an aryl iodide.

5. The method of claim 4, wherein the aryl halide is selected from the group consisting of bromobenzene; 4-bromobenzotrifluoride; 3-bromobenzotrifluoride; 1-bromo-3,5-diflurobenzene; 4-bromobenzofluoride; 1-bromo-3-(trifluoromethyl)benzene; 1-bromo-3-chlorobenzene; 4-bromobenzamide; 1-bromo-4-methylbenzene; 1-bromo-4-methoxybenzene; 1-bromo-3-methoxybenzene; 1-bromo-3,5-dimethoxybenzene; 4-bromobenzonitrile; methyl 4-bromobenzoate; 1-(4-bromophenyl)ethan-1-one; 3-bromopyridine; 5-bromopyrimidine; chlorobenzene; 4-chlorobenzotrifluoride; 3-chlorobenzotrifluoride; 1-chloro-3,5-diflurobenzene; 4-chlorobenzofluoride; 1-chloro-3-(trifluoromethyl)benzene; 1-chloro-3-chlorobenzene; 4-chlorobenzamide; 1-chloro-4-methylbenzene; 1-chloro-4-methoxybenzene; 1-chloro-3-methoxybenzene; 1-chloro-3,5-dimethoxybenzene; 4-chlorobenzonitrile; methyl 4-chlorobenzoate; 1-(4-chlorophenyl)ethan-1-one; 3-chloropyridine; 5-chloropyrimidine; iodobenzene; 4-iodobenortrifluoride; 3-iodobenzotrifluoride; 1-iodo-3,5-diflurobenzene; 4-iodobenzofluoride; 1-iodo-3-(trifluoromethyl)benzene; 1-iodo-3-chlorobenzene; 4-iodobenzamide; 1-iodo-4-methylbenzene; 1-iodo-4-methoxybenzene; 1-iodo-3-methoxybenzene; 1-iodo-3,5-dimethoxybenzene; 4-iodobenzonitrile; methyl 4-iodobenzoate; 1-(4-bromophenyl)ethan-1-one; 3-iodopyridine; and 5-iodopyrimidine.

6. The method of claim 1, wherein the amine is a primary amine or a secondary amine.

7. The method of claim 6, wherein the amine is selected from the group consisting of propylamine, cyclohexylamine, phenethylamine, pyridine-3-amine, furan-2-ylmethanamine, aniline, 4-fluoroaniline, pyrrolidine, piperidine, morpholine, 4-methyl-piperidine, piperdine-4-ol, piperidine-4-carbonitrile, methyl piperidine-4-carboxylate, cyclohexanamine, 3-aminopyridine, propan-1-amine, hexan-1-amine, and 2-phenylethan-1-amine.

8. The method of claim 1, wherein the amine is present in a molar excess of the aryl halide present in the reaction mixture.

9. The method of claim 8, wherein the amine is present in about 1.8 to about 5.5 molar excess of the aryl halide present in the reaction mixture.

10. The method of claim 1, wherein the Ni(II) salt catalyst solution comprises an Ni(II) salt compound selected from a Nickel(II) bromide salt, glyme, or solvate; Nickel(II) chloride salt, glyme, or solvate; Nickel(II) fluoride salt, glyme, or solvate; or Nickel(II) iodide salt, glyme, or solvate; or combination thereof.

11. The method of claim 10, wherein the Ni(II) salt compound is selected from the group consisting of $NiBr_2$.glyme, $NiCl_2$.$6H_2O$, $NiCl_2$.glyme, and $NiBr_2$. $3H_2O$.

12. The method of claim 10, wherein the Ni(II) salt compound is $NiBr_2$.$3H_2O$.

13. The method of claim 10, wherein the Ni salt catalyst solution further comprises a polar solvent, and the Ni(II) salt compound is dissolved in the polar solvent.

14. The method of claim 13, where the polar solvent is selected from the group consisting of N,N-dimethylacetamide, dimethyl sulfoxide, methanol, N,N-dimethylformamide, and acetonitrile.

15. The method of claim 14, wherein the polar solvent is N,N-dimethylacetamide.

16. The method of claim 1, wherein the optional additional base is selected from the group consisting of quinuclidine, morpholine, N,N-diisopropylethylamine, and triethylamine.

17. The method of claim 16, wherein the optional additional base is quinuclidine.

18. The method of claim 1, wherein the light is at about 365 nm or 405 nm.

19. A method for forming an aryl carbon-nitrogen bond, the method comprising:
    contacting an aryl halide with at least about a 1.8 molar excess of an amine relative to the aryl halide, in the presence of a $NiBr_2 \cdot 3H_2O$ salt, optionally quinuclidine, and N,N-dimethylacetamide, thereby forming a reaction mixture, and
    exposing the reaction mixture to light at about 365 nm or 405 nm under reaction conditions sufficient to form the aryl carbon-nitrogen bond;
    wherein the formation of the aryl carbon-nitrogen bond is light-driven and Ni-catalyzed without the addition of a photoredox catalyst under said reaction conditions.

20. The method of claim 19, wherein the reactions conditions comprise holding the reaction mixture under light exposure at between about room temperature and about 80° C. for between about 1 hour and about 20 hours such that at least about 50% reaction yield is obtained.

21. The method of claim 9, wherein the amine is present in molar excess of the aryl halide such that reaction mixture does not include the optional additional base.

22. The method of claim 19, wherein the amine is present in molar excess of the aryl halide such that the reaction mixture does not include the optional quinuclidine.

23. The method of claim 3, wherein the formation of the aryl carbon-nitrogen bond is tolerant to oxygen and water in the reaction mixture such that the at least about 80% reaction yield is obtained under reactions conditions that comprise providing an oxygen sparge prior to light exposure to increase oxygen content of the reaction mixture, the use of a hydrated Ni(II) salt catalyst solution to provide water content to the reaction mixture, and combinations thereof.

* * * * *

UNITED STATES PATENT AND TRADEMARK OFFICE
CERTIFICATE OF CORRECTION

PATENT NO. : 11,104,653 B2
APPLICATION NO. : 16/404255
DATED : August 31, 2021
INVENTOR(S) : Miyake et al.

Page 1 of 1

It is certified that error appears in the above-identified patent and that said Letters Patent is hereby corrected as shown below:

In the Claims

Claim 5, Column 40, Lines 29-30, delete "4-iodobenortrifluoride" and replace with --4-iodobenzotrifluoride--.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*